US012624006B2

(12) United States Patent
Dumeunier et al.

(10) Patent No.: US 12,624,006 B2
(45) Date of Patent: May 12, 2026

(54) PROCESS FOR THE PREPARATION OF 5-(1-CYANOCYCLOPROPYL)-PYRIDINE-2-CARBOXYLIC ACID ESTERS AMIDES AND NITRILES

(71) Applicant: SYNGENTA CROP PROTECTION AG, Basel (CH)

(72) Inventors: Raphael Dumeunier, Stein (CH); Renaud Beaudegnies, Stein (CH); Martin Pouliot, Stein (CH); Alexander Gaspers, Stein (CH)

(73) Assignee: SYNGENTA CROP PROTECTION AG, Basel (CH)

( * ) Notice: Subject to any disclaimer, the term of this patent is extended or adjusted under 35 U.S.C. 154(b) by 482 days.

(21) Appl. No.: 18/248,289

(22) PCT Filed: Oct. 8, 2021

(86) PCT No.: PCT/EP2021/077899
§ 371 (c)(1),
(2) Date: Apr. 7, 2023

(87) PCT Pub. No.: WO2022/074214
PCT Pub. Date: Apr. 14, 2022

(65) Prior Publication Data

US 2023/0382866 A1 Nov. 30, 2023

(30) Foreign Application Priority Data

Oct. 9, 2020 (EP) .................................... 20201119

(51) Int. Cl.

| | |
|---|---|
| ***C07D 213/84*** | (2006.01) |
| ***C07D 213/79*** | (2006.01) |
| ***C07D 213/803*** | (2006.01) |
| ***C07D 213/81*** | (2006.01) |
| ***C07D 409/04*** | (2006.01) |

(52) U.S. Cl.
CPC ......... *C07D 213/84* (2013.01); *C07D 213/79* (2013.01); *C07D 213/803* (2013.01); *C07D 213/81* (2013.01); *C07D 409/04* (2013.01)

(58) Field of Classification Search
CPC .................................................... C07D 213/84
See application file for complete search history.

(56) References Cited

FOREIGN PATENT DOCUMENTS

| | | | | | |
|---|---|---|---|---|---|
| JP | 2018012664 | A | * | 1/2018 | |
| WO | WO-2010077565 | A2 | * | 7/2010 | ............. C08G 73/22 |
| WO | 2018/077565 | A1 | | 5/2018 | |
| WO | 2018108726 | A1 | | 6/2018 | |
| WO | 2019234158 | A1 | | 12/2019 | |

OTHER PUBLICATIONS

Wislicenus, J. "Adolph Strecker's Short Textbook of Organic Chemistry" 1881, Spottiswoode: London, pp. 38-39.*
Cherng, Yie-Jia "Synthesis of substituted pyridines by the reactions of halopyridines with sulfur, oxygen and carbon nucleophiles under focused microwave irradiation." Tetrahedron (2002), 58(24), 4931-4935.*
Maruoka "Ring Opening of 2-ACYLAMINO-4,5 DIHYDRO-3-FURANCARBONITRILES By Use of Titanium (IV) Chloride" Heterocycles, vol. 31, No. 11 , 1990, 2011-2023.*
EPO; App. No. EP 20201119.3; Extended European Search Report mailed Mar. 2, 2021; pp. 1-5.
WIPO; App. No. PCT/EP2021/077899; International Search Report and Written Opinion mailed Dec. 14, 2021; pp. 1-10.

* cited by examiner

*Primary Examiner* — David K O'Dell
(74) *Attorney, Agent, or Firm* — BakerHostetler; Toni-Junell Herbert

(57) ABSTRACT

A process for the preparation of compound of formula I is provided: Formula (I) where $R_1$ and $R_2$ are as defined in the description.

(I)

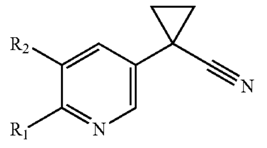

20 Claims, No Drawings

PROCESS FOR THE PREPARATION OF 5-(1-CYANOCYCLOPROPYL)-PYRIDINE-2-CARBOXYLIC ACID ESTERS AMIDES AND NITRILES

CROSS-REFERENCE TO RELATED APPLICATIONS

This application is a U.S. National Stage Application, filed under 35 U.S.C. § 371, of International Application No. PCT/EP2021/077899, filed Oct. 8, 2021, which claims priority to EP 20201119.3, filed Oct. 9, 2020, the entire contents of which are incorporated by reference herein.

The present invention relates to the preparation of 5-(1-cyanocyclopropyl)-pyridine-2-carboxylic acid esters amides and nitriles that are useful as intermediates for the preparation of agrochemicals.

Certain 5-(1-cyanocyclopropyl)-pyridine-2-carboxylic acids with 3-alkylsulfanyl substituents (and certain corresponding esters, amides and salts thereof) are useful intermediates for the preparation of biologically active compounds in the agrochemical industries as previously described, for example, in: WO16087265, WO16121997, WO2019059244, WO2020071304, WO2020090585 and JP2020079325.

Known synthesis of 5-(1-cyanocyclopropyl)-pyridine-2-carboxylic acids with 3-alkylsulfanyl substituents involve many reaction steps. For example, a route to access the 3-ethylsulfanyl derivative have been reported from methyl 5-bromo-3-ethylsulfanyl-pyridine-2-carboxylate (in WO 2018/077565) and is shown in Scheme 1

Scheme 1. Route to 5-(1-cyanocyclopropyl)-3-ethylsulfanyl-pyridine-2-carboxylic acid

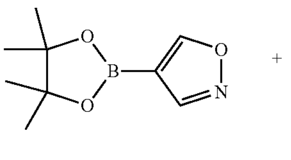

-continued

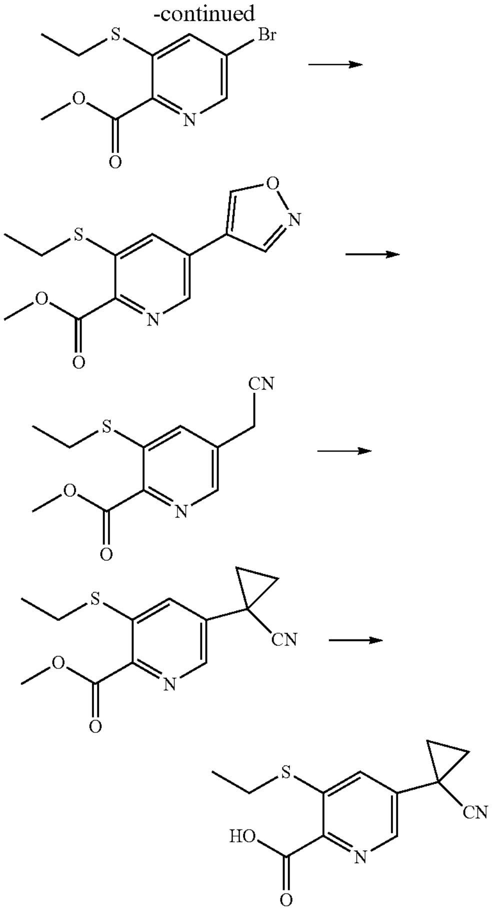

Two routes to access alkyl 5-bromo-3-ethylsulfanyl-pyridine-2-carboxylate have been reported (route A: CN105218437; route B: US2012/0165338 or *J. Org. Chem.* 2009, 74, 4547-4553) and are shown in Scheme 2 ($R_1$ is H, $C_1$-$C_4$alkyl, or an alkali metal ion)

Scheme 2. Routes to alkyl 5-bromo-3-ethylsulfanyl-pyridine-2-carboxylate

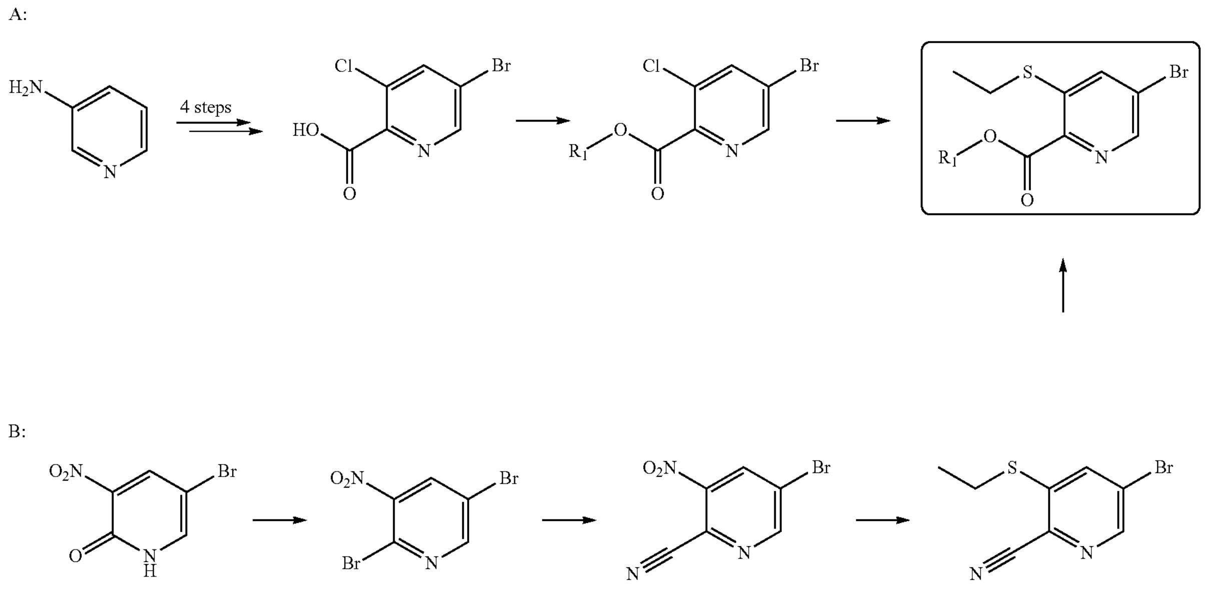

-continued

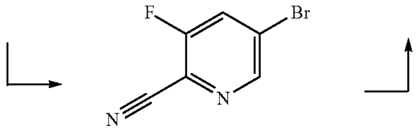

Such long and laborious syntheses are not suitable for preparing large amount of material due to low overall yields and large amount of waste generated. Therefore, it would be advantageous to have available a more efficient and economical route to these useful intermediates.

The present invention therefore provides a process for the preparation of 5-(1-cyanocyclopropyl)-pyridine-2-carboxylic acids esters amides and nitriles of formula I or agrochemically acceptable salts thereof (I)

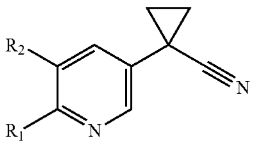

wherein $R_1$ is —$CO_2R_4$, —$CO(NR_5R_6)$, carboxylate or cyano; $R_2$ is hydrogen, halogen or —$SR_3$; $R_3$ is $C_1$-$C_4$alkyl or $C_3$-$C_6$cycloalkyl-$C_1$-$C_4$alkyl; $R_4$ is hydrogen, —$Si(CH_3)_3$ or $C_1$-$C_6$alkyl; and $R_5$ and $R_6$ are, independently from each other, hydrogen or $C_1$-$C_4$alkyl.

In accordance with a first aspect of the present invention, the direct replacement of a halogen atom in 5-position of pyridines of formula (III), using a base and a reagent of formula (IV) yields a compound of formula (I) wherein $R_1$ and $R_2$ are defined as previously and Hal is halogen (Scheme 3).

Scheme 3

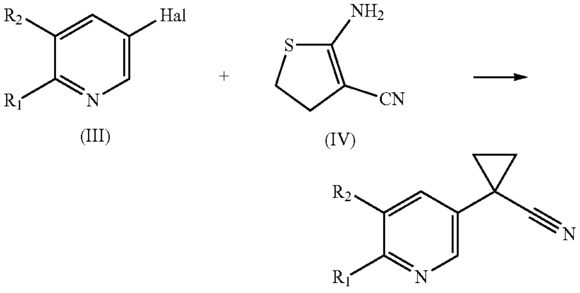

(III) (IV) (I)

The compound of formula (IV) is known, commercially available and its synthesis described by Yamagata, Kenji et al in *Chemical & Pharmaceutical Bulletin,* 30(12), 4396-401; 1982; or by Wamhoff, Heinrich and Thiemig, Heinz Albrecht in *Chemische Berichte,* 118(11), 4473-85; 1985; or by Caspari, Philip et al in *RSC Advances,* 6(100), 98059-98065; 2016.

Thus, according to another aspect of the present invention, there is provided a process for the preparation of compounds of formula I (Scheme 4):

(I)

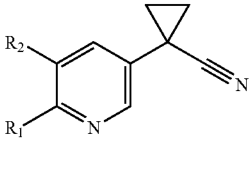

wherein $R_1$ is —$CO_2R_4$, —$CO(NR_5R_6)$, carboxylate or cyano; $R_2$ is hydrogen, halogen or —$SR_3$; $R_3$ is $C_1$-$C_4$alkyl or $C_3$-$C_6$cycloalkyl-$C_1$-$C_4$alkyl; $R_4$ is hydrogen, —$Si(CH_3)_3$ or $C_1$-$C_6$alkyl; and $R_5$ and $R_6$ are, independently from each other, hydrogen or $C_1$-$C_4$alkyl, or an agrochemically acceptable salt of a compound of formula I; which process comprises:

reacting a compound of formula (III)

(III)

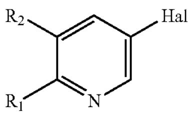

wherein $R_1$ and $R_2$ are defined as under formula I above and Hal is halogen with a compound of formula (IV), (IV)

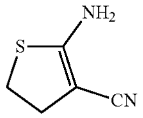

in the presence of a suitable base, in an appropriate solvent (or diluent);

to produce a compound of formula (I) or an agrochemically acceptable salt thereof.

Another aspect of the present invention provides certain compounds of formula I represented by the compounds of formula Ia (Ia)

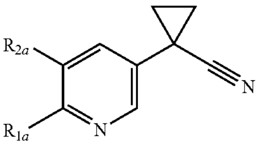

wherein $R_{1a}$ is —$CO_2R_{4a}$, —$CO(NR_{5a}R_{6a})$, carboxylate or cyano; $R_{2a}$ is hydrogen, halogen or —$SR_{3a}$; $R_{3a}$ is $C_1$-$C_4$alkyl or $C_3$-$C_6$cycloalkyl-$C_1$-$C_4$alkyl; $R_{4a}$ is hydrogen, —$Si(CH_3)_3$ or $C_1$-$C_6$alkyl; and $R_{5a}$ and $R_{6a}$ are, independently from each other, hydrogen or $C_1$-$C_4$alkyl, or an agrochemically acceptable salt of a compound of formula Ia;

with the proviso that the compound of formula Ia is not: selected from the group consisting of a compound of the formula Ib, Ic and Id;

(Ib)

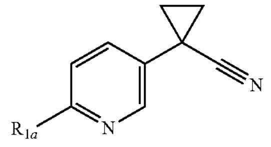

wherein $R_{1b}$ is CN or —$CO_2Me$;

(Ic)

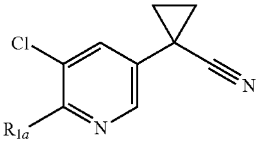

wherein $R_{1c}$ is —$CO_2H$, —$CO_2Me$, —$CO_2Et$ or —CONHMe; and (Id)

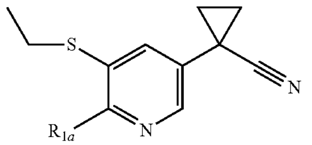

wherein $R_{1d}$ is —$CO_2H$, —$CO_2Me$ or —CONHMe.

The process of the present invention is demonstrated to be of great usefulness as it allows the synthesis of key building blocks for the preparation of agrochemicals in higher yields and with more favorable conditions with respect to previously described routes.

Compounds of formula I that are prepared by the inventive process, or compounds of formula III which are used in the inventive process, that have at least one basic centre can form, for example, acid addition salts, for example with strong inorganic acids such as mineral acids, for example perchloric acid, sulfuric acid, nitric acid, nitrous acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I, or compounds of formula III which are used in the inventive process, which have at least one acidic group can form, for example, salts with bases, for example mineral salts such as alkali metal or alkaline earth metal salts, for example sodium, potassium, lithium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine. In a preferred embodiment, compounds of formula III which are used in the inventive process are either neutral or are negatively charged, particularly when the substituent $R_1$ is a carboxylate anion.

In each case, the compounds of formula (I) that are prepared by the process according to the invention are in free form or in salt form, e.g. an agronomically usable salt form.

The term "$C_1$-$C_n$alkyl" as used herein refers to a saturated straight-chain or branched hydrocarbon radical attached via any of the carbon atoms having 1 to n carbon atoms, for example, any one of the radicals methyl, ethyl, n-propyl, 1-methylbutyl, 2-methylbutyl, 3-methylbutyl, 2,2-dimethylpropyl, 1-ethylpropyl, n-hexyl, n-pentyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "$C_3$-$C_6$cycloalkyl" as used herein refers to 3-6 membered cycloalkyl groups such as cyclopropane, cyclobutane, cyclopentane and cyclohexane.

The suffix "—$C_1$-$C_4$alkyl" after terms such as "$C_3$-$C_6$cycloalkyl" as used herein refers to a straight chain or branched saturated alkyl radical which is substituted by $C_3$-$C_6$cycloalkyl. An example of $C_3$-$C_6$cycloalkyl-$C_1$-$C_4$alkyl is for example, cyclopropylmethyl.

Halogen is generally fluorine, chlorine, bromine or iodine.

Additional aspects of the process according to the invention for making compounds of formula (I) are further detailed and explained by reference to scheme 5, wherein $R_1$, $R_2$ and Hal are defined as above. Some intermediates compounds are made and further transformed in the process of making compounds of formula (I), which can then be detailed as passing through the following intermediates in a single pot operation (Scheme 5)

Scheme 5

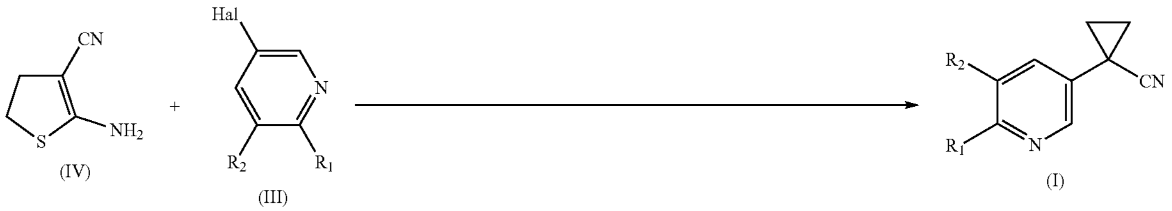

(IV) (III) (I)

-continued

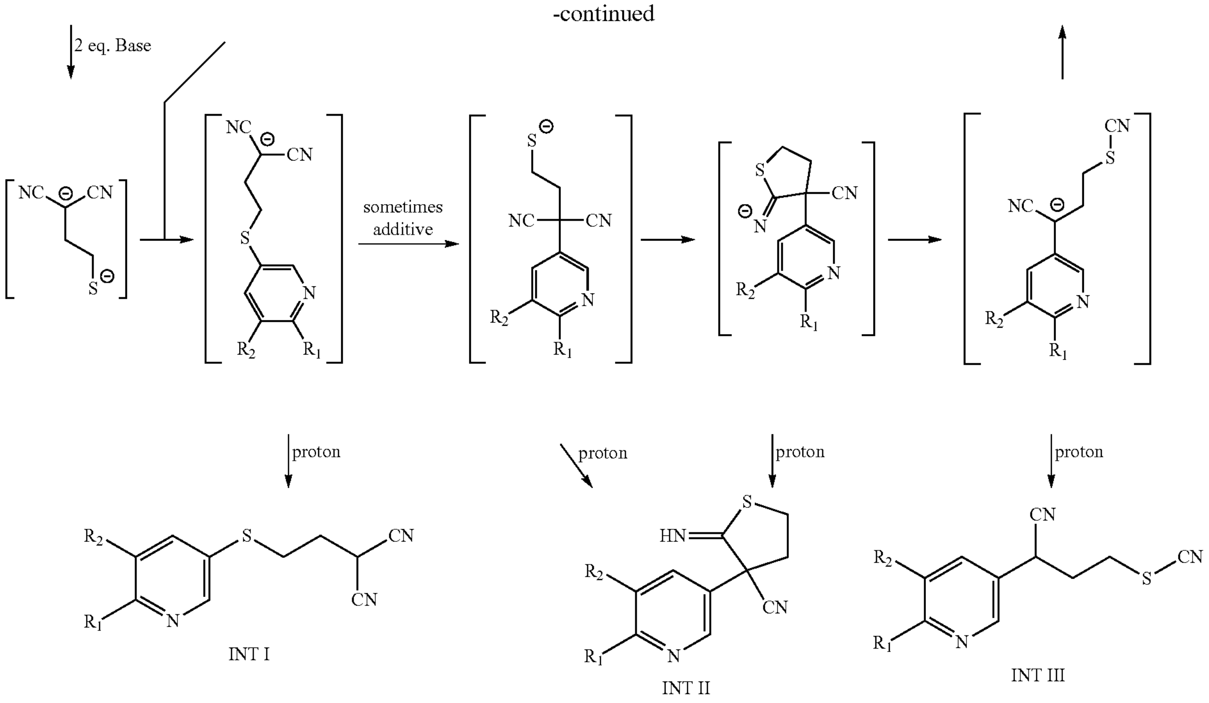

The intermediate salts can sometimes be protonated, isolated and characterized under the forms of INT I, INT II, or INT III before their complete transformations into compounds of formula (I). In this regard, the compounds INT I, INT II, or INT III can also be resubmitted to basic conditions in a separate, subsequent step to provide compounds of formula (I). In the process according to the invention for making compounds of formula (I), examples of suitable bases are alkali metal hexamethyldisilazides, alkaline earth metal hexamethyldisilazides, alkali metal hydroxides, alkali metal alkoxides or alkaline earth metal alkoxides. Examples which may be mentioned are sodium hydroxide, potassium hydroxide, sodium methanolate, sodium tertiobutanolate, and potassium tertiobutanolate; preferably an alkali metal hydroxide, more preferably sodium hydroxide. In one embodiment, for intermediate I (INT I), a special case of $R_1$ being carboxylate anion requires the cations to partly or fully consist of magnesium or zinc cations for the final steps of the reaction to proceed (such as those shown in scheme 5). Such a base as magnesium bis(tertio-butanolate) or magnesium bis(hexamethyldisilazide) can then be used from the start without any additives being necessary. Alternatively, bases such as sodium or potassium hydroxides or alkoxides can be used when followed by the addition of magnesium$^{(II)}$, zinc$^{(II)}$ or Al$^{(III)}$ salts as additives, such as for example $MgCl_2$, $ZnCl_2$, $Al(OtBu)_3$ or $AlCl_3$ (referred to in scheme 5 as "sometimes additive").

Such additives can be introduced into the reaction after the formation of INT I or, in some cases, from the start of the reaction. An example of the latter is the concomitant use of NaOtBu (as base) and $Al(OtBu)_3$ (as additive) from the start of the reaction. The water or the alcohol generated from the base, after generation of INT I during the reaction, can advantageously be removed from the reaction mixture by distillation before the introduction of the additive. This can be done without solvent removal if the solvent used has high boiling point (such as NMP or DMSO), or with removal of only a fraction of the solvent if the boiling point comes closer to the alcohol or water (DMF). Removing the water or the alcohol from the reaction mixture before introduction of the additive allows the use of reduced amounts of the latter. In a preferred embodiment, the reaction will also proceed without removal (continuous or after INT I formation) of water or alcohol provided that sufficient equivalents of additive are introduced.

The following Table X is intended to illustrate some combinations of bases, solvents and/or additives within the scope of the present invention. Preferably, if an additive is used, it is introduced into the reaction after the formation of INT I.

TABLE X

| Entry | Base | Solvent | Additive | Temp | Yield of Compoud (I) |
|---|---|---|---|---|---|
| 1 | Solid NaOMe | NMP | $MgCl_2$ | 65° C. | 87% |
| 2 | Solid NaOtBu | NMP | $MgCl_2$ | 65° C. | 90% (example 11) |
| 3 | NaOH powder | DMF | $MgCl_2$ | 65° C. | 91% |
| 4 | NaOH powder | DMSO | $ZnCl_2$ | 65° C. | circa 70% |
| 5 | $Mg(OtBu)_2$ | DMF | — | 65° C. | 58% |
| 6 | $Mg(HMDS)_2$ | DMF | — | 65° C. | 72% |
| 7 | LiHMDS | DMF | $Al(OtBu)_3$ | 65° C. | 49% |
| 8 | Solid NaOtBu | NMP | $AlCl_3$ | 65° C. | circa 70% |

A preferred embodiment of the process for the preparation of compounds of formula I as shown and explained in scheme 5 is further detailed by reference to scheme 6. In particular, alternatives to the use of magnesium(II), zinc(II) or aluminium (III) additives for preparation of compounds of formula I by the inventive process are for example, the addition of trimethylsilylchloride (TMSCl) after distillation of the water or alcohol generated during the formation of INT I. This creates a silyl ester in situ from INT I (Si-INT I) which is activated enough to engage spontaneously into the further transformations to the next silylated intermediates Si-INT-II and Si-INT-III, all the way to a silylated ester analogue of a compound of formula (In scheme 6, a silylated ester analogue of a compound of formula I is represented by a silylated ester analogue of a compound of formula I-1). The latter is cleaved spontaneously during the aqueous work-up of the reaction to finally deliver compound I-1, as depicted in Scheme 6:

Scheme 6

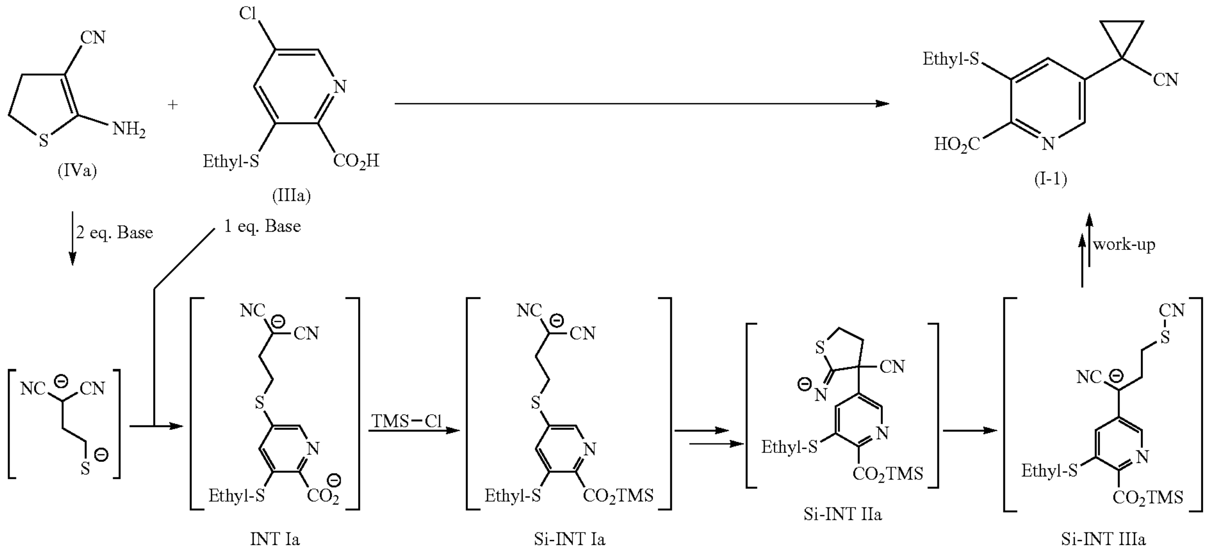

In the process according to the invention of making compounds of formula (I), appropriate solvents (or diluents) are polar solvents, such as dimethylformamide, dimethylsulfoxide, N-methyl-pyrrolidine, dimethylacetamide, sulfolane, N,N'-dimethylpropyleneurea (DMPU); more preferably polar organic solvents chosen from dimethylformamide, dimethylsulfoxide, N-methyl-pyrrolidine.

In one embodiment, in the process according to the invention of making compounds of formula (I), the reaction is advantageously carried out in a temperature range from approximately 0° C. to approximately +100° C., preferably from approximately +20° C. to approximately +80° C.

Another preferred embodiment of the process for the preparation of compounds of formula I as shown and explained in scheme 5 is further detailed by reference to scheme 7 which shows specific embodiments of the formulae I, III, INT 1, INT II and INT III as represented by compounds of formulae I-1, IIIa, INT Ia, INT IIa and INT IIIa, respectively.

Scheme 7

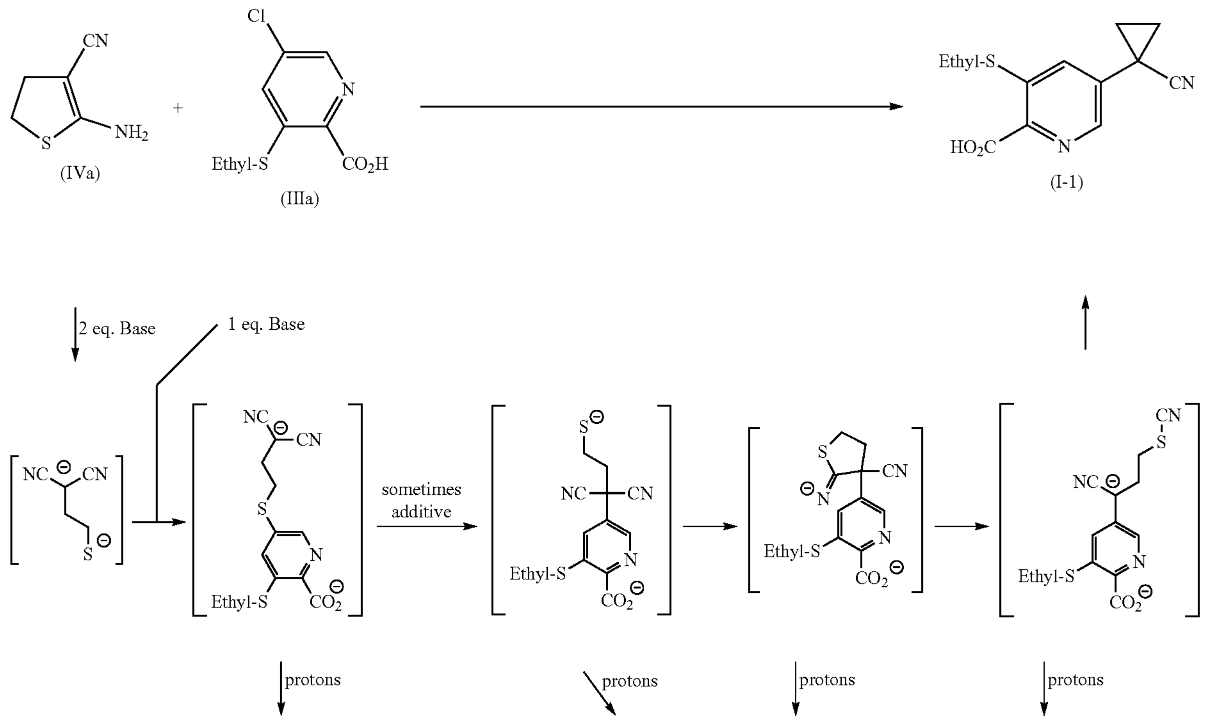

-continued

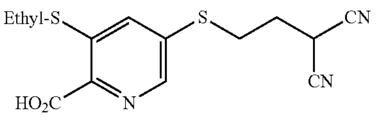

INT Ia

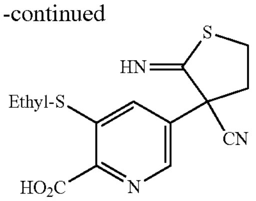

INT IIa

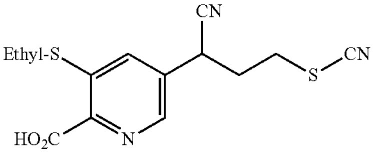

INT IIIa

In one embodiment, the anions of INT I are intermediates which often do accumulate to a reasonable extent during the course of the reaction, so that if the reaction is interrupted before completion, INT I can be isolated and purified, as can be seen in the preparatory examples. In particular, if the first steps to anions of INT I are run at lower temperature (room temperature or even −10° C. to −20° C.), a good yield of INT I can be achieved, if it is wished to interrupt the reaction at this stage. A special case is INT Ia (with $R_1$ being carboxylic acid), as the anions of the latter will accumulate completely as long as no cations such as Mg(II), Zn(II) or Al(III) are present in the reaction mixture. An excellent yield in isolating INT Ia can then be achieved if desired (see example 18).

In another embodiment, anions of INT II and INT III do not accumulate to significant levels in the reaction mixture. In some cases, they can be observed by in situ monitoring or (their protonated forms) by LCMS of reactions samples, but their amounts are too low to be able to interrupt the reaction, isolate and characterize pure samples of INT II or INT III. For getting proper analysis and pure samples of those intermediates, a specific synthesis can be made to properly characterize them, for example by following the steps described in scheme 8 for getting INT IIa and INT IIIa Scheme 8 (examples 21 and 22 of the preparatory section below)

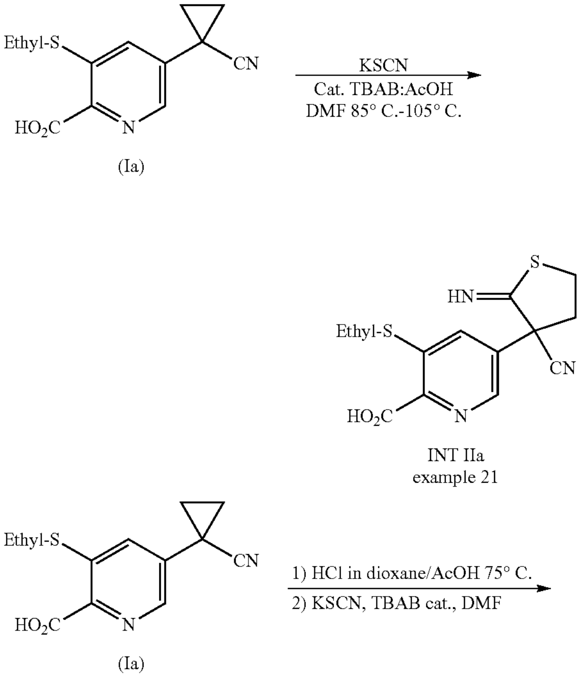

(Ia)

INT IIa
example 21

(Ia)

-continued

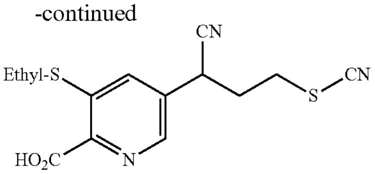

INT IIIa
example 22

In another aspect, the present invention also relates to compounds of the formula INT I

INT I

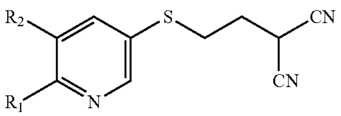

wherein $R_1$ and $R_2$ are defined as under formula I above, or an agrochemically acceptable salt of a compound of formula INT I.

In a preferred group of compounds of formula INT I, $R_1$ is —$CO_2R_4$, —$CONH_2$, carboxylate or cyano; wherein $R_4$ is hydrogen, —$Si(CH_3)_3$, methyl, ethyl, isopropyl, tert-butyl, or sec-butyl; and $R_2$ is hydrogen, halogen or —$SR_3$; wherein $R_3$ is ethyl or cyclopropyl methyl; preferably, $R_2$ is hydrogen, chloro or —$SR_3$; wherein $R_3$ is ethyl.

Another group of compounds according to the invention are those of the formula INT II

INT II

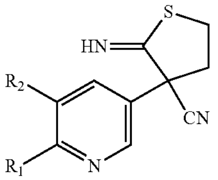

wherein $R_1$ and $R_2$ are defined as under formula I above, or an agrochemically acceptable salt of a compound of formula INT II.

In a preferred group of compounds of formula INT II, $R_1$ is —$CO_2R_4$, —$CONH_2$, carboxylate or cyano; wherein $R_4$ is hydrogen, —$Si(CH_3)_3$, methyl, ethyl, isopropyl, tert-butyl, or sec-butyl; and $R_2$ is hydrogen, halogen or —$SR_3$; wherein $R_3$ is ethyl or cyclopropyl methyl; preferably, $R_2$ is hydrogen, chloro or —$SR_3$; wherein $R_3$ is ethyl.

Another group of compounds according to the invention are those of the formula INT III

INT III

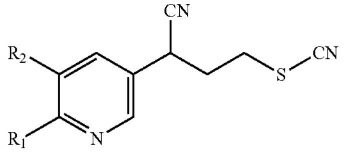

wherein $R_1$ and $R_2$ are defined as under formula I above, or an agrochemically acceptable salt of a compound of formula INT III.

In a preferred group of compounds of formula INT II, $R_1$ is $—CO_2R_4$, $—CONH_2$, carboxylate or cyano; wherein $R_4$ is hydrogen, $—Si(CH_3)_3$, methyl, ethyl, isopropyl, tert-butyl, or sec-butyl; and $R_2$ is hydrogen, halogen or $—SR_3$; wherein $R_3$ is ethyl or cyclopropyl methyl; preferably, $R_2$ is hydrogen, chloro or $—SR_3$; wherein $R_3$ is ethyl.

Certain preferred embodiments according to the invention are provided as set out below.

Embodiment 1 provides a process for the preparation of a compound of formula I by reacting a compound of formula III with a compound of formula IVa, as defined in scheme 3 above.

Embodiment 2 provides a process for the preparation of a compound of formula I by reacting a compound of formula III with a compound of formula IV, as defined in scheme 4 above.

Embodiment 3 provides a process for the preparation of a compound of formula I by reacting a compound of formula III with a compound of formula IV, as defined in scheme 5 above.

Embodiment 4 provides a process for the preparation of a compound of formula I by reacting a compound of formula IIIa with a compound of formula IVa, as defined in scheme 6 above.

Embodiment 5 provides a process for the preparation of a compound of formula I by reacting a compound of formula IIIa with a compound of formula IVa, as defined in scheme 7 above.

Embodiment 6 provides compounds of formula INT I, as defined above.

Embodiment 7 provides compounds of formula INT II, as defined above.

Embodiment 8 provides compounds of formula INT III, as defined above.

Embodiment 9 provides compounds of formula I represented by the compounds of formula Ia, as defined above.

With respect to embodiments 1-8, preferred values of $R_1$, $R_2$, $R_3$, $R_4$, $R_5$, $R_6$ and Hal are (as applicable), in any combination thereof, as set out below:

Preferably $R_1$ is $—CO_2R_4$, $—CO(NR_5R_6)$ or cyano; wherein $R_4$ is hydrogen or $C_1$-$C_6$alkyl; and $R_5$ and $R_6$ are, independently from each other, hydrogen or $C_1$-$C_4$alkyl.

More preferably, $R_1$ is $—CO_2R_4$, $—CO(NR_5R_6)$ or cyano; wherein $R_4$ is hydrogen or $C_1$-$C_4$alkyl; and $R_5$ and $R_6$ are, independently from each other, hydrogen or methyl.

Also preferred is when $R_1$ is $—CO_2R_4$, $—CONH_2$ or cyano; wherein $R_4$ is hydrogen, methyl, ethyl, isopropyl, tert-butyl, $Si(CH_3)_3$ or sec-butyl.

Further preferred is when $R_1$ is $—CO_2H$, $—CONH_2$ or a cyano group.

Most preferably $R_1$ is $—CO_2H$ or, in case of a salt, a carboxylate anion thereof.

Preferably, agrochemically acceptable salts are alkali metal or alkaline earth metal salts.

More preferably, agrochemically acceptable salts are sodium, potassium, lithium or magnesium salts.

Most preferably, agrochemically acceptable salts are sodium, magnesium or lithium.

Also preferred when $R_1$ is a carboxylate anion of $—CO_2H$, is that the corresponding cations partly or fully consist of magnesium.

Preferably, $R_2$ is hydrogen, halogen or $—SR_3$; wherein $R_3$ is $C_1$-$C_4$alkyl or $C_3$-$C_6$cycloalkyl-$C_1$-$C_4$alkyl; preferably, wherein $R_3$ is ethyl or cyclopropyl methyl.

More preferably, $R_2$ is hydrogen, halogen or $—SR_3$; wherein $R_3$ is ethyl or cyclopropyl methyl; preferably, $R_2$ is hydrogen, chloro or $—SR_3$; wherein $R_3$ is ethyl.

Most preferably, $R_2$ is $—SR_3$; wherein $R_3$ is ethyl.

Preferably, Hal is halogen.

More preferably, Hal is fluoro, chloro or bromo.

Also preferred is when Hal is chloro or bromo.

Most preferably, Hal is chloro.

With respect to embodiment 9, $R_{1a}$ and $R_{2a}$ are defined as under formula Ia above, and preferred values of $R_{1a}$ and $R_{2a}$ are as set out below.

Preferably when $R_{2a}$ is hydrogen, $R_{1a}$ is $CO_2Et$, $CO_2iPr$, $CO_2sBu$, $CO_2tBu$, $CO_2H$, $CONH_2$, or $CO_2Si(CH_3)_3$.

Preferably when $R_{2a}$ is chloro, $R_{1a}$ is CN, $CO_2iPr$, $CO_2sBu$, $CO_2tBu$, $CONH_2$ or $CO_2Si(CH_3)_3$.

Preferably when $R_{2a}$ is —SEt, $R_{1a}$ is CN, $CO_2Et$, $CO_2iPr$, $CO_2sBu$, $CO_2tBu$, $CONH_2$ or $CO_2Si(CH_3)_3$. The examples which follow in Tables A, B, C, D and E below are intended to illustrate the invention and show preferred compounds of formulae I, III, INT I, INT II and INT III that can be used and/or prepared according to the process described above. In the tables below, "Me" represents methyl; "Et" represents ethyl; "iPr" represents isopropyl; "sBu" represents sec-butyl; "tBu" represents tert-butyl.

The following table A illustrates specific compounds of formula III:

TABLE A

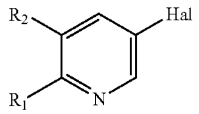

(III)

| Compound of Formula III | $R_1$ | $R_2$ | Hal |
|---|---|---|---|
| 1 | CN | H | F |
| 2 | $CO_2Me$ | H | F |
| 3 | $CO_2Et$ | H | F |
| 4 | $CO_2iPr$ | H | F |
| 5 | $CO_2sBu$ | H | F |
| 6 | $CO_2tBu$ | H | F |
| 7 | $CO_2H$ | H | F |
| 8 | $CONH_2$ | H | F |
| 9 | $CO_2Si(CH_3)_3$ | H | F |
| 10 | CN | H | Cl |
| 11 | $CO_2Me$ | H | Cl |
| 12 | $CO_2Et$ | H | Cl |
| 13 | $CO_2iPr$ | H | Cl |
| 14 | $CO_2sBu$ | H | Cl |
| 15 | $CO_2tBu$ | H | Cl |
| 16 | $CO_2H$ | H | Cl |
| 17 | $CONH_2$ | H | Cl |
| 18 | $CO_2Si(CH_3)_3$ | H | Cl |
| 19 | CN | H | Br |
| 20 | $CO_2Me$ | H | Br |
| 21 | $CO_2Et$ | H | Br |
| 22 | $CO_2iPr$ | H | Br |
| 23 | $CO_2sBu$ | H | Br |

TABLE A-continued (III)

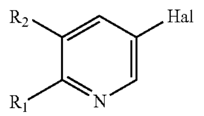

| Compound of Formula III | $R_1$ | $R_2$ | Hal |
|---|---|---|---|
| 24 | $CO_2tBu$ | H | Br |
| 25 | $CO_2H$ | H | Br |
| 26 | $CONH_2$ | H | Br |
| 27 | $CO_2Si(CH_3)_3$ | H | Br |
| 28 | CN | $SCH_2CH_3$ | F |
| 29 | $CO_2Me$ | $SCH_2CH_3$ | F |
| 30 | $CO_2Et$ | $SCH_2CH_3$ | F |
| 31 | $CO_2iPr$ | $SCH_2CH_3$ | F |
| 32 | $CO_2sBu$ | $SCH_2CH_3$ | F |
| 33 | $CO_2tBu$ | $SCH_2CH_3$ | F |
| 34 | $CO_2H$ | $SCH_2CH_3$ | F |
| 35 | $CONH_2$ | $SCH_2CH_3$ | F |
| 36 | $CO_2Si(CH_3)_3$ | $SCH_2CH_3$ | F |
| 37 | CN | $SCH_2CH_3$ | Cl |
| 38 | $CO_2Me$ | $SCH_2CH_3$ | Cl |
| 39 | $CO_2Et$ | $SCH_2CH_3$ | Cl |
| 40 | $CO_2iPr$ | $SCH_2CH_3$ | Cl |
| 41 | $CO_2sBu$ | $SCH_2CH_3$ | Cl |
| 42 | $CO_2tBu$ | $SCH_2CH_3$ | Cl |
| 43 | $CO_2H$ | $SCH_2CH_3$ | Cl |
| 44 | $CONH_2$ | $SCH_2CH_3$ | Cl |
| 45 | $CO_2Si(CH_3)_3$ | $SCH_2CH_3$ | Cl |
| 46 | CN | $SCH_2CH_3$ | Br |
| 47 | $CO_2Me$ | $SCH_2CH_3$ | Br |
| 48 | $CO_2Et$ | $SCH_2CH_3$ | Br |
| 49 | $CO_2iPr$ | $SCH_2CH_3$ | Br |
| 50 | $CO_2sBu$ | $SCH_2CH_3$ | Br |
| 51 | $CO_2tBu$ | $SCH_2CH_3$ | Br |
| 52 | $CO_2H$ | $SCH_2CH_3$ | Br |
| 53 | $CONH_2$ | $SCH_2CH_3$ | Br |
| 54 | $CO_2Si(CH_3)_3$ | $SCH_2CH_3$ | Br |
| 55 | CN | Cl | F |
| 56 | $CO_2Me$ | Cl | F |
| 57 | $CO_2Et$ | Cl | F |
| 58 | $CO_2iPr$ | Cl | F |
| 59 | $CO_2sBu$ | Cl | F |
| 60 | $CO_2tBu$ | Cl | F |
| 62 | $CO_2H$ | Cl | F |
| 62 | $CONH_2$ | Cl | F |
| 63 | $CO_2Si(CH_3)_3$ | Cl | F |
| 64 | CN | Cl | Cl |
| 65 | $CO_2Me$ | Cl | Cl |
| 66 | $CO_2Et$ | Cl | Cl |
| 67 | $CO_2iPr$ | Cl | Cl |
| 68 | $CO_2sBu$ | Cl | Cl |
| 69 | $CO_2tBu$ | Cl | Cl |
| 70 | $CO_2H$ | Cl | Cl |
| 71 | $CONH_2$ | Cl | Cl |
| 72 | $CO_2Si(CH_3)_3$ | Cl | Cl |
| 73 | CN | Cl | Br |
| 74 | $CO_2Me$ | Cl | Br |
| 75 | $CO_2Et$ | Cl | Br |
| 76 | $CO_2iPr$ | Cl | Br |
| 77 | $CO_2sBu$ | Cl | Br |
| 78 | $CO_2tBu$ | Cl | Br |
| 79 | $CO_2H$ | Cl | Br |
| 80 | $CONH_2$ | Cl | Br |
| 81 | $CO_2Si(CH_3)_3$ | Cl | Br |

and the agrochemically acceptable salts of the compounds of formula III in Table A (and in the case of compounds where $R_1$ is —$CO_2H$, including the sodium, potassium, magnesium or lithium salts (i.e., wherein $R_1$ is a carboxylate anion)).

The following table B illustrates specific compounds of formula INT I:

TABLE B

INT I

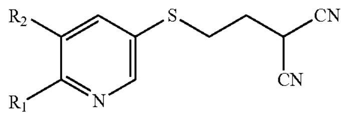

| Compound of formula INT I | $R_1$ | $R_2$ |
|---|---|---|
| 1 | CN | H |
| 2 | $CO_2Me$ | H |
| 3 | $CO_2Et$ | H |
| 4 | $CO_2iPr$ | H |
| 5 | $CO_2sBu$ | H |
| 6 | $CO_2tBu$ | H |
| 7 | $CO_2H$ | H |
| 8 | $CONH_2$ | H |
| 9 | $CO_2Si(CH_3)_3$ | H |
| 10 | CN | $SCH_2CH_3$ |
| 11 | $CO_2Me$ | $SCH_2CH_3$ |
| 12 | $CO_2Et$ | $SCH_2CH_3$ |
| 13 | $CO_2iPr$ | $SCH_2CH_3$ |
| 14 | $CO_2sBu$ | $SCH_2CH_3$ |
| 15 | $CO_2tBu$ | $SCH_2CH_3$ |
| 16 | $CO_2H$ | $SCH_2CH_3$ |
| 17 | $CONH_2$ | $SCH_2CH_3$ |
| 18 | $CO_2Si(CH_3)_3$ | $SCH_2CH_3$ |
| 19 | CN | Cl |
| 20 | $CO_2Me$ | Cl |
| 21 | $CO_2Et$ | Cl |
| 22 | $CO_2iPr$ | Cl |
| 23 | $CO_2sBu$ | Cl |
| 24 | $CO_2tBu$ | Cl |
| 25 | $CO_2H$ | Cl |
| 26 | $CONH_2$ | Cl |
| 27 | $CO_2Si(CH_3)_3$ | Cl |

and the agrochemically acceptable salts of the compounds of formula INT I in Table B (and in the case of compounds where $R_1$ is —$CO_2H$, including the sodium, potassium, magnesium or lithium salts (i.e., wherein $R_1$ is a carboxylate anion)).

The following table C illustrates specific compounds of formula INT II:

TABLE C

INT II

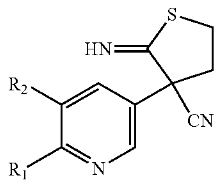

| Compound of Formula INT II | $R_1$ | $R_2$ |
|---|---|---|
| 1 | CN | H |
| 2 | $CO_2Me$ | H |
| 3 | $CO_2Et$ | H |
| 4 | $CO_2iPr$ | H |
| 5 | $CO_2sBu$ | H |
| 6 | $CO_2tBu$ | H |
| 7 | $CO_2H$ | H |
| 8 | $CONH_2$ | H |
| 9 | $CO_2Si(CH_3)_3$ | H |
| 10 | CN | $SCH_2CH_3$ |
| 11 | $CO_2Me$ | $SCH_2CH_3$ |
| 12 | $CO_2Et$ | $SCH_2CH_3$ |

TABLE C-continued

INT II

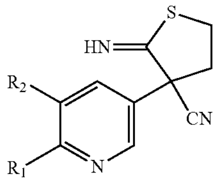

| Compound of Formula INT II | $R_1$ | $R_2$ |
|---|---|---|
| 13 | $CO_2iPr$ | $SCH_2CH_3$ |
| 14 | $CO_2sBu$ | $SCH_2CH_3$ |
| 15 | $CO_2tBu$ | $SCH_2CH_3$ |
| 16 | $CO_2H$ | $SCH_2CH_3$ |
| 17 | $CONH_2$ | $SCH_2CH_3$ |
| 18 | $CO_2Si(CH_3)_3$ | $SCH_2CH_3$ |
| 19 | CN | Cl |
| 20 | $CO_2Me$ | Cl |
| 21 | $CO_2Et$ | Cl |
| 22 | $CO_2iPr$ | Cl |
| 23 | $CO_2sBu$ | Cl |
| 24 | $CO_2tBu$ | Cl |
| 25 | $CO_2H$ | Cl |
| 26 | $CONH_2$ | Cl |
| 27 | $CO_2Si(CH_3)_3$ | Cl |

and the agrochemically acceptable salts of the compounds of formula INT II in Table C (and in the case of compounds where $R_1$ is —$CO_2H$, including the sodium, potassium, magnesium or lithium salts (i.e., wherein $R_1$ is a carboxylate anion)).

The following table D illustrates specific compounds of formula INT III:

TABLE D

INT III

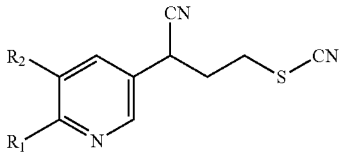

| Compound of Formula INT III | $R_1$ | $R_2$ |
|---|---|---|
| 1 | CN | H |
| 2 | $CO_2Me$ | H |
| 3 | $CO_2Et$ | H |
| 4 | $CO_2iPr$ | H |
| 5 | $CO_2sBu$ | H |
| 6 | $CO_2tBu$ | H |
| 7 | $CO_2H$ | H |
| 8 | $CONH_2$ | H |
| 9 | $CO_2Si(CH_3)_3$ | H |
| 10 | CN | $SCH_2CH_3$ |
| 11 | $CO_2Me$ | $SCH_2CH_3$ |
| 12 | $CO_2Et$ | $SCH_2CH_3$ |
| 13 | $CO_2iPr$ | $SCH_2CH_3$ |
| 14 | $CO_2sBu$ | $SCH_2CH_3$ |
| 15 | $CO_2tBu$ | $SCH_2CH_3$ |
| 16 | $CO_2H$ | $SCH_2CH_3$ |
| 17 | $CONH_2$ | $SCH_2CH_3$ |
| 18 | $CO_2Si(CH_3)_3$ | $SCH_2CH_3$ |
| 19 | CN | Cl |
| 20 | $CO_2Me$ | Cl |
| 21 | $CO_2Et$ | Cl |
| 22 | $CO_2iPr$ | Cl |
| 23 | $CO_2sBu$ | Cl |
| 24 | $CO_2tBu$ | Cl |

TABLE D-continued

INT III

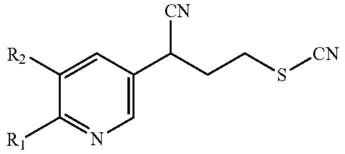

| Compound of Formula INT III | $R_1$ | $R_2$ |
|---|---|---|
| 25 | $CO_2H$ | Cl |
| 26 | $CONH_2$ | Cl |
| 27 | $CO_2Si(CH_3)_3$ | Cl |

and the agrochemically acceptable salts of the compounds of formula INT III in Table D (and in the case of compounds where $R_1$ is —$CO_2H$, including the sodium, potassium, magnesium or lithium salts (i.e., wherein $R_1$ is a carboxylate anion)).

The following table E illustrates specific compounds of formula I:

TABLE E (I)

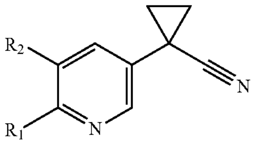

| Compound of formula I | $R_1$ | $R_2$ |
|---|---|---|
| 1 | CN | H |
| 2 | $CO_2Me$ | H |
| 3 | $CO_2Et$ | H |
| 4 | $CO_2iPr$ | H |
| 5 | $CO_2sBu$ | H |
| 6 | $CO_2tBu$ | H |
| 7 | $CO_2H$ | H |
| 8 | $CONH_2$ | H |
| 9 | $CO_2Si(CH_3)_3$ | H |
| 10 | CN | $SCH_2CH_3$ |
| 11 | $CO_2Me$ | $SCH_2CH_3$ |
| 12 | $CO_2Et$ | $SCH_2CH_3$ |
| 13 | $CO_2iPr$ | $SCH_2CH_3$ |
| 14 | $CO_2sBu$ | $SCH_2CH_3$ |
| 15 | $CO_2tBu$ | $SCH_2CH_3$ |
| 16 | $CO_2H$ | $SCH_2CH_3$ |
| 17 | $CONH_2$ | $SCH_2CH_3$ |
| 19 | $CO_2Si(CH_3)_3$ | $SCH_2CH_3$ |
| 19 | CN | Cl |
| 20 | $CO_2Me$ | Cl |
| 21 | $CO_2Et$ | Cl |
| 22 | $CO_2iPr$ | Cl |
| 23 | $CO_2sBu$ | Cl |
| 24 | $CO_2tBu$ | Cl |
| 25 | $CO_2H$ | Cl |
| 26 | $CONH_2$ | Cl |
| 27 | $CO_2Si(CH_3)_3$ | Cl |

and the agrochemically acceptable salts of the compounds of formula I in Table E (and in the case of compounds where $R_1$ is —$CO_2H$, including the sodium, potassium, magnesium or lithium salts (i.e., wherein $R_1$ is a carboxylate anion)).

PREPARATORY EXAMPLES

Purity of starting materials, crudes and products was determined with quantitative $^1H$ NMR using 1,3,5-trimethoxy benzene as an internal standard.

Example 1: Preparation of 5-(1-cyanocyclopropyl)pyridine-2-carbonitrile

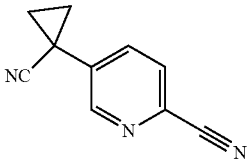 [SMILES: N#Cc1ccc(C2(C#N)CC2)cn1]

To a solution of 5-amino-2,3-dihydrothiophene-4-carbonitrile (0.1 g, 0.79 mmol) in DMF (3.2 mL) was added 5-chloropyridine-2-carbonitrile (0.11 g, 0.79 mmol) and sodium tertio-butanolate (0.152 g, 1.585 mmol). The reaction mixture was stirred at ambient temperature for 3 hours, then at 65° C. for one hour more, before being allowed to cool down to room temperature. The reaction mixture was poured onto aqueous saturated ammonium chloride (10 mL), acidified with 1M HCl (10 mL) and extracted four times with dichloromethane (4×30 mL). The combined organic layers were dried over solid anhydrous Magnesium sulfate, filtered and evaporated under reduced pressure. QNMR indicated a chemical yield of 78%. The crude was purified by column chromatography to obtain the title compound in 74% isolated yield (99.3 mg). $^1H$ NMR (400 MHz, $CDCl_3$): δ (ppm)=8.61 (dd, J=2.6, 0.7 Hz, 1H), 7.80-7.74 (m, 1H), 7.73-7.65 (m, 1H), 1.99-1.91 (m, 2H), 1.60-1.53 (m, 2H)

Example 2: Preparation of 5-(1-cyanocyclopropyl)-3-ethylsulfanyl-pyridine-2-carbonitrile

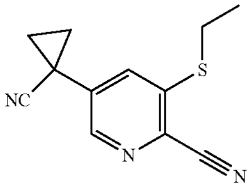 [SMILES: CCSc1cc(C2(C#N)CC2)cnc1C#N]

To a solution of 5-bromo-3-ethylsulfanyl-pyridine-2-carbonitrile (0.2 g, 0.823 mmol) and 5-amino-2,3-dihydrothiophene-4-carbonitrile (0.135 g, 92.4% w/w purity, 0.987 mmol) in DMF (1.64 mL) was added dropwise a solution of Sodium bis(trimethylsilyl)amide (1M in THF, 1.6 mL, 1.6 mmol) at room temperature. The reaction mixture was stirred 1 h before being quenched with aqueous saturated ammonium chloride (5 mL) and extracted three times with ethyl acetate (3×20 mL). The combined organic layers were washed with brine (20 mL), dried over solid anhydrous Magnesium sulfate, filtered and evaporated under reduced pressure yielding a brownish oil (219.3 mg). QNMR indicated a strength of 39.4% w/w, leading to a chemical yield of 46%. $^1H$ NMR (400 MHz, d6-DMSO) δ ppm 1.26-1.32 (m, 3H) 1.77-1.83 (m, 2H) 1.88-1.95 (m, 2H) 3.15-3.26 (m, 2H) 7.75-7.77 (d, J=2.20 Hz, 1H) 8.50 (d, J=2.20 Hz, 1H) LC-MS: ret.: 0.90 min, m/z $+H^+$: 230

Example 3: Preparation of 3-chloro-5-(1-cyanocyclopropyl)pyridine-2-carbonitrile

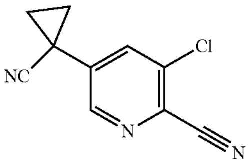 [SMILES: N#Cc1ncc(C2(C#N)CC2)cc1Cl]

To a solution of 3,5-dichloropyridine-2-carbonitrile (0.3 g, 1.734 mmol) and 5-amino-2,3-dihydrothiophene-4-carbonitrile (0.255 g, 94.3% w/w purity, 1.907 mmol) in DMF (2.6 mL) was added dropwise a solution of Sodium bis (trimethylsilyl)amide (1 M in THF, 3.8 mL, 3.8 mmol) at room temperature. The reaction mixture was stirred 2 h before being quenched with aqueous saturated ammonium chloride (5 mL) and extracted three times with ethyl acetate (3×30 mL). The combined organic layers were washed with brine (15 mL), dried over solid Sodium sulfate, filtered and evaporated under reduced pressure yielding a brownish oil (436.8 mg). QNMR indicated a strength of 18.4% w/w, leading to a chemical yield of 23%. $^1H$ NMR (400 MHz, d6-DMSO) δ ppm 1.80-1.84 (m, 2H) 1.93-1.98 (m, 2H) 8.13 (d, J=1.83 Hz, 1H) 8.72 (d, J=1.83 Hz, 1H) LC-MS: ret.: 0.81 min, m/z $+H^+$: 204/206

Example 4: Preparation of methyl 5-(1-cyanocyclopropyl)-3-ethylsulfanyl-pyridine-2-carboxylate

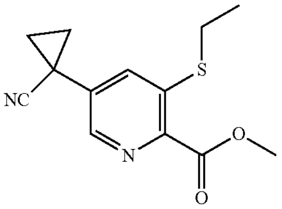 [SMILES: CCSc1cc(C2(C#N)CC2)cnc1C(=O)OC]

To a solution of methyl 5-bromo-3-ethylsulfanyl-pyridine-2-carboxylate (0.3 g, 1.086 mmol) and 5-amino-2,3-dihydrothiophene-4-carbonitrile (0.144 g, 1.141 mmol) in DMF (4.34 mL) was added dropwise a solution of Sodium bis(trimethylsilyl)amide (1M in THF, 2.17 mL, 2.17 mmol) at room temperature. The reaction mixture was stirred 4 h 20 before being quenched with aqueous saturated ammonium chloride (10 mL) and extracted three times with methyl tButyl ether (3×20 mL). The combined organic layers were washed twice with water (2×10 mL), then brine (10 mL), dried over solid Sodium sulfate, filtered and evaporated under reduced pressure yielding a yellow oil (287 mg). QNMR indicated a strength of 61% w/w, leading to a chemical yield of 61%. $^1H$ NMR (400 MHz, CDCl3) δ ppm 1.43 (t, J=7.34 Hz, 3H) 1.55-1.60 (m, 2H) 1.86-1.93 (m, 2H) 3.00 (q, J=7.34 Hz, 2H) 4.00-4.02 (m, 3H) 7.72 (d, J=2.20 Hz, 1H) 8.16 (d, J=2.20 Hz, 1H) LC-MS: ret.: 0.85 min, m/z $+H^+$: 263

Example 5: Preparation of ethyl 5-(1-cyanocyclopropyl)pyridine-2-carboxylate

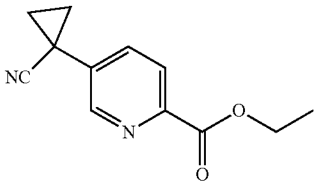 [SMILES: CCOC(=O)c1ccc(C2(C#N)CC2)cn1]

To a solution of ethyl 5-chloropyridine-2-carboxylate (0.098 g, 0.527 mmol) and 5-amino-2,3-dihydrothiophene-4-carbonitrile (0.066 g, 0.527 mmol) in DMF (2.11 mL) was added dropwise a solution of Sodium bis(trimethylsilyl) amide (1M in THF, 1.05 mL, 1.05 mmol) at room temperature. The reaction mixture was stirred overnight at room temperature then 4 h at 65° C. before being allowed to cool down to room temperature. It was then quenched with aqueous saturated ammonium chloride (10 mL), acidified with aqueous 1N HCl (10 mL) and extracted five times with dichloromethane (5×30 mL). The combined organic layers were dried over solid Sodium sulfate, filtered and evaporated under reduced pressure yielding an oil. QNMR indicated a chemical yield of 35%. The crude was purified by column chromatography to obtain the title compound as a white solid (38 mg) in 34% isolated yield. $^1$H NMR (400 MHz, $CDCl_3$): δ (ppm)=8.62 (d, J=1.8 Hz, 1H), 8.11 (d, J=8.1 Hz, 1H), 7.76 (dd, J=8.1, 2.6 Hz, 1H), 4.47 (q, J=7.0 Hz, 2H), 1.97-1.80 (m, 2H), 1.62-1.47 (m, 2H), 1.43 (t, J=7.2 Hz, 3H)

Example 6: Preparation of ethyl 5-(1-cyanocyclopropyl)-3-ethylsulfanyl-pyridine-2-carboxylate

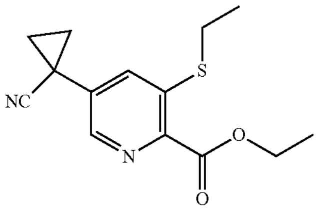 [SMILES: CCOC(=O)c1ncc(C2(C#N)CC2)cc1SCC]

To a solution of ethyl 5-chloro-3-ethylsulfanyl-pyridine-2-carboxylate (0.1 g, 0.372 mmol) and 5-amino-2,3-dihydrothiophene-4-carbonitrile (0.049 g, 0.391 mmol) in DMF (1.5 mL) was added dropwise a solution of Sodium bis (trimethylsilyl)amide (1M in THF, 0.74 mL, 0.74 mmol) at room temperature. The reaction mixture was stirred 3 h 30 before being quenched with aqueous saturated ammonium chloride (5 mL) and extracted three times with methyl tButyl ether (3×10 mL). The combined organic layers were washed twice with water (2×10 mL), then brine (2×10 mL), dried over solid Sodium sulfate, filtered and evaporated under reduced pressure yielding a yellow oil (113 mg). QNMR indicated a strength of 66% w/w, leading to a chemical yield of 66%. $^1$H NMR (400 MHz, CDCl3) δ ppm 1.40-1.47 (m, 6H) 1.54-1.58 (m, 2H) 1.88-1.93 (m, 2H) 3.00 (q, J=7.34 Hz, 2H) 4.48 (q, J=7.34 Hz, 2H) 7.72 (d, J=2.20 Hz, 1H) 8.18 (d, J=2.20 Hz, 1H)

Example 7: Preparation of ethyl 3-chloro-5-(1-cyanocyclopropyl)pyridine-2-carboxylate

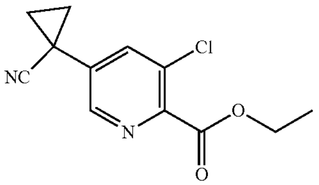 [SMILES: CCOC(=O)c1ncc(C2(C#N)CC2)cc1Cl]

To a solution of ethyl 3,5-dichloropyridine-2-carboxylate (0.25 g, 94.7% w/w purity, 1.08 mmol) and 5-amino-2,3-dihydrothiophene-4-carbonitrile (0.143 g, 1.13 mmol) in DMF (4.3 mL) was added dropwise a solution of Sodium bis(trimethylsilyl)amide (1M in THF, 2.15 mL, 2.15 mmol) at room temperature. The reaction mixture was stirred overnight before being quenched with aqueous saturated ammonium chloride (10 mL) and extracted three times with methyl tButyl ether (3×20 mL). The combined organic layers were washed twice with brine (2×20 mL), dried over solid Sodium sulfate, filtered and evaporated under reduced pressure yielding a brownish oil (301 mg). QNMR indicated a strength of 47% w/w, leading to a chemical yield of 52%. $^1$H NMR (400 MHz, CDCl3) δ ppm 1.44 (t, J=7.15 Hz, 3H) 1.53-1.57 (m, 2H) 1.89-1.95 (m, 2H) 4.48 (q, J=7.34 Hz, 2H) 7.74 (d, J=2.20 Hz, 1H) 8.47 (d, J=1.83 Hz, 1H). LC-MS: ret.: 0.87 min, m/z $+H^+$: 251/253

Example 8: Preparation of isopropyl 3-chloro-5-(1-cyanocyclopropyl)pyridine-2-carboxylate

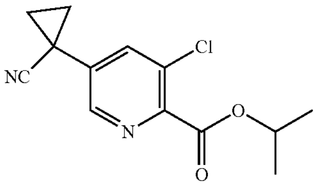 [SMILES: CC(C)OC(=O)c1ncc(C2(C#N)CC2)cc1Cl]

To a solution of isopropyl 3,5-dichloropyridine-2-carboxylate (0.1 g, 98% w/w purity, 0.419 mmol) and 5-amino-2,3-dihydrothiophene-4-carbonitrile (0.057 g, 98% w/w purity, 0.44 mmol) in DMF (1.7 mL) was added dropwise a solution of Lithium bis(trimethylsilyl)amide (1M in THF, 0.84 mL, 0.84 mmol) at room temperature. The reaction mixture was stirred at this temperature for 2 h 45 then at 50° C. for 30 min, before being allowed to cool down to room temperature. It was then quenched with aqueous saturated ammonium chloride (5 mL) and extracted three times with ethyl acetate (3×15 mL). The combined organic layers were washed twice brine (2×20 mL), dried over solid Sodium sulfate, filtered and evaporated under reduced pressure yielding a dark oil (440 mg). QNMR indicated a strength of 12% w/w, leading to a chemical yield of 49%. $^1$H NMR (400 MHz, CDCl3) δ ppm 1.39 (d, J=6.24 Hz, 6H) 1.50-1.53 (m, 2H) 1.85-1.89 (m, 2H) 5.31 (hept, J=6.24 Hz, 1H) 7.69 (d, J=2.20 Hz, 1H) 8.43 (d, J=1.83 Hz, 1H).

Example 9: Preparation of tert-butyl 5-(1-cyanocyclopropyl)pyridine-2-carboxylate

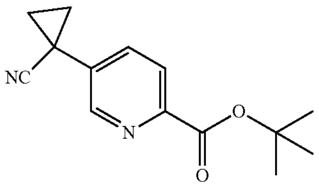 [SMILES: CC(C)(C)OC(=O)c1ccc(C2(C#N)CC2)cn1]

To a solution of tert-butyl 5-chloropyridine-2-carboxylate (0.169 g, 0.792 mmol) and 5-amino-2,3-dihydrothiophene-4-carbonitrile (0.1 g, 0.792 mmol) in DMF (3.1 mL) was added dropwise a solution of Sodium bis(trimethylsilyl) amide (1M in THF, 1.58 mL, 1.58 mmol) at room temperature. The reaction mixture was stirred at this temperature for 6 h. It was then quenched with aqueous saturated ammonium chloride (10 mL), acidified with aqueous 1N HCl (10 mL) and extracted four times with dichloromethane (4×30 mL). The combined organic layers were dried over solid magnesium sulfate, filtered and evaporated under reduced pressure yielding a brown solid. QNMR indicated a chemical yield of 70%. The crude was purified by column chromatography to obtain the title compound as a pale solid (128 mg) in 66% isolated yield. $^1H$ NMR (400 MHz, $CDCl_3$): δ (ppm)=8.60 (d, J=2.6 Hz, 1H), 8.02 (d, J=7.7 Hz, 1H), 7.75 (dd, J=8.3, 2.4 Hz, 1H), 1.90-1.85 (m, 2H), 1.62 (s, 9H), 1.55-1.49 (m, 2H).

Example 10: Preparation of tert-butyl 3-chloro-5-(1-cyanocyclopropyl)pyridine-2-carboxylate

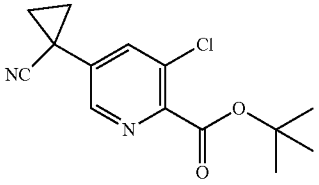 [SMILES: CC(C)(C)OC(=O)c1ncc(C2(C#N)CC2)cc1Cl]

To a solution of tert-butyl 3,5-dichloropyridine-2-carboxylate (0.3 g, 82% w/w purity, 0.993 mmol) and 5-amino-2,3-dihydrothiophene-4-carbonitrile (0.134 g, 94.3% w/w purity, 1 mmol) in DMF (4 mL) was added dropwise a solution of potassium tert-butanolate (1.6M in THF, 1.4 mL, 2.18 mmol) at 0° C. The reaction mixture was stirred at this temperature for 1 h then at room temperature for 2 h 30 min, then at 40° C. for before being allowed to cool down to room temperature. It was then quenched with aqueous saturated ammonium chloride (5 mL) and extracted three times with ethyl acetate (3×20 mL). The combined organic layers were washed with brine (10 mL), dried over solid Sodium sulfate, filtered and evaporated under reduced pressure yielding a dark oil (0.417 g). QNMR indicated a strength of 20% w/w, leading to a chemical yield of 30%. $^1H$ NMR (400 MHz, d6-DMSO) δ ppm 1.56 (s, 9H) 1.70-1.80 (m, 1H) 1.83-1.90 (m, 1H) 7.97 (d, J=1.83 Hz, 1H) 8.59 (d, J=1.83 Hz, 1H).

Example 11: Preparation of 5-(1-cyanocyclopropyl)-3-ethylsulfanyl-pyridine-2-carboxylic acid

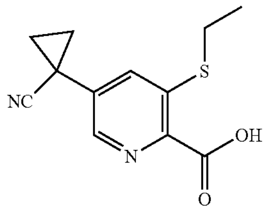 [SMILES: CCSc1cc(C2(C#N)CC2)cnc1C(=O)O]

To a suspension of tBuONa (6.42 g, 64.8 mmol) in NMP (17.3 mL) heated at 65° C. was added a solution of 5-chloro-3-ethylsulfanyl-pyridine-2-carboxylic acid (5 g, 94.1% w/w purity, 21.6 mmol) and 5-amino-2,3-dihydrothiophene-4-carbonitrile (3.43 g, 95.4% w/w purity, 25.9 mmol) in NMP (21.6 mL) over a period of 1 h. After the end of addition, the mixture was stirred 20 minutes before an extra portion of NaOtBu (1.61 g, 16.2 mmol) was added. After one hour, still at 65° C., a short path distilling apparatus was fitted to the round bottom flask, (with Vigreux), the pressure was reduced to 20 mbar and the mixture was stirred for an extra 1 h at 65° C. (while distillation of the tBuOH occurred). After being allowed to come back at atmospheric pressure, a solution of $MgCl_2$ (3.23 g, 54 mmol) in NMP (17.3 mL) was added in 5 minutes to the hot reaction mixture. After 1 h, the mixture was allowed to cool down to room temperature; 50 mL of 1N aq. NaOH and 50 mL of water were added. The mixture was transferred to a separatory funnel and washed with TBME (100 mL). The phases were separated, and the aqueous layer was then acidified to pH 1.5 with 1N HCl, and extracted three times with EtOAc (3×300 mL). The combined organic layers (from EtOAc extractions) were dried over anhydrous sodium sulfate, filtered and evaporated under reduced pressure. 6 mL of d6-DMSO were added to homogenize the concentrate to a clear, dark brown liquid (24.57 g). Purity was measured by 1H-QNMR twice; to give a strength of 19.7% (therefore a chemical yield of 90%). The solution was then dropped onto ice cold water under stirring; a beige precipitate appeared and was collected (4.758 g). Purity was measured to be 84% w/w; the isolated yield was therefore of 82%.

Alternatively, the same product can be obtained from 5-(3,3-dicyanopropylsulfanyl)-3-ethylsulfanyl-pyridine-2-carboxylic acid:

To a solution of 5-(3,3-dicyanopropylsulfanyl)-3-ethylsulfanyl-pyridine-2-carboxylic acid (5.2 mmol) in of NMP was added a 50% aq. NaOH solution (0.728 mL, 13.8 mmol). The two phases were mixed vigorously for 30 min then the flask was transferred to the rotavap, heated at 50° C. under vacuum to remove the water. After this operation, extra NMP was added (5.2 mL) and the mixture was heated at 65° C. $MgCl_2$ (1 g, 10.41 mmol) was then added in one portion and the reaction was stirred at for 3 h. An extra portion of $MgCl_2$ was then added (0.25 g, 2.6 mmol) and the mixture was stirred for 30 min at 65° C. before being allowed to cool down to room temperature. The mixture was diluted with 1M NaOH, then acidified until pH 6-7 with 2N HCl before ethyl acetate was added. The pH of the aqueous was further lowered to 1.5 by addition of 2N HCl, the phases were separated and the aqueous phase was extracted three times with ethyl acetate. The combined organic layers were dried over anhydrous sodium sulfate, filtered and evaporated under reduced pressure. A dark oil (4.37 g) was obtained. Purity was measured by 1H-QNMR; to give a strength of 26% (therefore a chemical yield of 88%). The solution was then dropped onto 75 mL of ice cold water under stirring; a beige precipitate appeared and was collected (1.173 g). Purity was measured to be 79% w/w; the isolated yield was therefore of 71%.

$^1$H NMR (400 MHz, d6-DMSO) δ ppm 1.25 (t, J=7.34 Hz, 3H) 1.68-1.76 (m, 2H) 1.81-1.89 (m, 2H) 3.02 (q, J=7.34 Hz, 2H) 7.62 (d, J=1.83 Hz, 1H) 8.36 (d, J=2.20 Hz, 1H)

LC-MS: m/z +H$^+$: 249

Example 12: Preparation of 3-chloro-5-(1-cyanocyclopropyl)pyridine-2-carboxylic acid

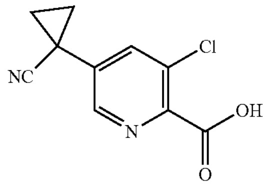 [SMILES: N#CC1(c2cnc(C(=O)O)c(Cl)c2)CC1]

To a solution of 5-bromo-3-chloro-pyridine-2-carboxylic acid (0.3 g, 1.269 mmol) and 5-amino-2,3-dihydrothiophene-4-carbonitrile (0.178 g, 94.3% w/w purity, 1.332 mmol) in DMF (2.5 mL) was added dropwise a solution of potassium tert-butanolate (1.7M in THF, 3 mL, 5.08 mmol) at room temperature. The reaction mixture was stirred at this temperature for 3 h, then solid Magnesium dichloride (0.169 g, 1.776 mmol) was added. The reaction mixture was stirred 1 h 20 min at 50° C. before being allowed to cool down to room temperature. It was then quenched with 2N aqueous HCl to pH 1 and extracted three times with ethyl acetate (3×20 mL). The combined organic layers were dried over solid Sodium sulfate, filtered and evaporated under reduced pressure yielding a dark oil (0.435 g). QNMR indicated a strength of 38.4% w/w, leading to a chemical yield of 59%. $^1$H NMR (400 MHz, d6-DMSO) δ ppm 1.71-1.76 (m, 2H) 1.83-1.88 (m, 2H) 7.93 (d, J=2.20 Hz, 1H) 8.58 (d, J=1.83 Hz, 1H) LC-MS: m/z +H$^+$: 223/225

Example 13: Preparation of 5-(1-cyanocyclopropyl)-3-ethylsulfanyl-pyridine-2-carboxamide

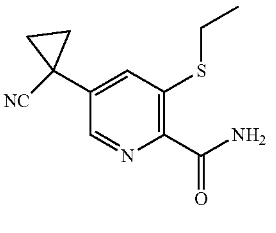 [SMILES: CCSc1cc(C2(C#N)CC2)cnc1C(N)=O]

A solution of 5-chloro-3-ethylsulfanyl-pyridine-2-carboxamide (0.2 g, 98% purity w/w, 0.905 mmol) and 5-amino-2,3-dihydrothiophene-4-carbonitrile (0.156 g, 95% w/w purity, 1.18 mmol) in DMF (3.6 mL) at 65° C. was added to a solution of Sodium tert-butanolate (0.179 g, 1.81 mmol) in 3.6 mL of DMF at 65° C. The reaction mixture was stirred at this temperature overnight. The compound can be characterized after standard work-up procedure. $^1$H NMR (400 MHz, d6-DMSO) δ ppm 1.26 (t, J=7.34 Hz, 3H) 1.70-1.74 (m, 2H) 1.84-1.87 (m, 2H) 2.95 (q, J=7.34 Hz, 2H) 7.57 (d, J=1.83 Hz, 1H) 7.57 (bs, 1H) 7.99 (bs, 1H) 8.28 (d, J=2.20 Hz, 1H)

Example 14: Preparation of 2-[2-[(6-cyano-5-ethylsulfanyl-3-pyridyl)sulfanyl]ethyl]propanedinitrile

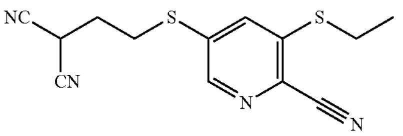 [SMILES: CCSc1cc(SCCC(C#N)C#N)cnc1C#N]

To a solution of 5-bromo-3-ethylsulfanyl-pyridine-2-carbonitrile (0.2 g, 0.823 mmol) and 5-amino-2,3-dihydrothiophene-4-carbonitrile (0.135 g, 92.4% w/w purity, 0.987 mmol) in DMF (3.2 mL) cooled at −20° C. was added dropwise a solution of potassium tert-butanolate (1.6M in THF, 1.1 mL, 1.727 mmol). The reaction mixture was stirred at this temperature for 1 h, then quenched with aqueous saturated ammonium chloride (5 mL) and extracted three times with ethyl acetate (3×20 mL). The combined organic layers were washed twice with brine (2×10 mL), dried over solid Sodium sulfate, filtered and evaporated under reduced pressure yielding a dark oil (0.288 g). QNMR indicated a strength of 47% w/w, leading to a chemical yield of 57%. $^1$H NMR (400 MHz, d6-DMSO) δ ppm 1.28 (t, J=7.34 Hz, 3H) 2.36-2.42 (m, 2H) 3.22 (q, J=7.34 Hz, 2H) 3.30-3.37 (m, 2H) 4.91 (t, J=6.79 Hz, 1H), 7.86 (d, J=1.83 Hz, 1H) 8.45 (d, J=1.83 Hz, 1H) LC-MS: m/z +H$^+$: 289

Example 15: Preparation of methyl 5-(3,3-dicyanopropylsulfanyl)-3-ethylsulfanyl-pyridine-2-carboxylate

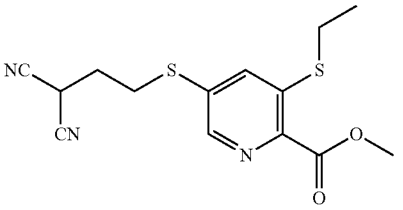 [SMILES: CCSc1cc(SCCC(C#N)C#N)cnc1C(=O)OC]

To a solution of methyl 5-bromo-3-ethylsulfanyl-pyridine-2-carboxylate (0.3 g, 1.086 mmol) and 5-amino-2,3-dihydrothiophene-4-carbonitrile (0.141 g, 1.12 mmol) in DMF (2.2 mL) cooled at 0° C. was added dropwise a solution of Sodium bis(trimethylsilyl)amide (1M in THF, 2.4 mL, 2.4 mmol). The reaction mixture was stirred at this temperature for 45 min, then quenched with aqueous saturated ammonium chloride (5 mL) and extracted three times with ethyl acetate (3×20 mL). The combined organic layers were washed twice with brine (2×10 mL), dried over solid Sodium sulfate, filtered and evaporated under reduced pressure yielding a dark oil (0.346 g). QNMR indicated a strength of 75% w/w, leading to a chemical yield of 74%. $^1$H NMR (400 MHz, d6-DMSO) δ ppm 1.25 (t, J=7.34 Hz, 3H) 2.35-2.41 (m, 2H) 3.05 (q, J=7.34 Hz, 2H) 3.29-3.34 (m, 2H) 3.85 (s, 3H) 4.93 (t, J=6.97 Hz, 1H) 7.73 (d, J=2.20 Hz, 1H) 8.35 (d, J=1.83 Hz, 1H) LC-MS: m/z +H$^+$: 322

Example 16: Preparation of ethyl 5-(3,3-dicyanopropylsulfanyl)-3-ethylsulfanyl-pyridine-2-carboxylate

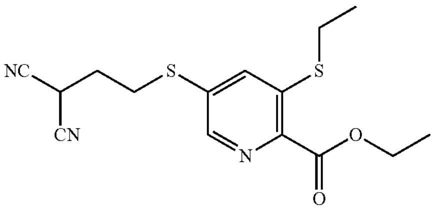 [SMILES: CCOC(=O)c1ncc(SCCC(C#N)C#N)cc1SCC]

To a solution of ethyl 5-chloro-3-ethylsulfanyl-pyridine-2-carboxylate (0.2 g, 0.814 mmol) and 5-amino-2,3-dihydrothiophene-4-carbonitrile (0.112 g, 96.3% w/w purity, 0.855 mmol) in DMF (3.2 mL) cooled at −20° C. was added dropwise a solution of Sodium bis(trimethylsilyl)amide (1M in THF, 1.8 mL, 1.8 mmol). The reaction mixture was stirred at this temperature for 1 h, then quenched with aqueous saturated ammonium chloride (5 mL) and extracted three times with ethyl acetate (3×20 mL). The combined organic layers were washed twice with brine (2×10 mL), dried over solid Sodium sulfate, filtered and evaporated under reduced pressure yielding a dark oil (0.316 g). QNMR indicated a strength of 47% w/w, leading to a chemical yield of 54%. $^1$H NMR (400 MHz, CDCl3) δ ppm 1.40 (t, J=7.34 Hz, 3H) 1.43-1.47 (t, 3H) 2.37 (q, J=7.09 Hz, 2H) 2.92-2.95 (m, 2H) 3.25-3.30 (m, 2H) 4.14-4.18 (t, 1H) 4.45-4.50 (m, 2H) 7.59 (d, J=2.20 Hz, 1H) 8.35 (d, J=2.20 Hz, 1H) LC-MS: m/z $+H^+$: 336

Example 17: Preparation of ethyl 3-chloro-5-(3,3-dicyanopropylsulfanyl)pyridine-2-carboxylate

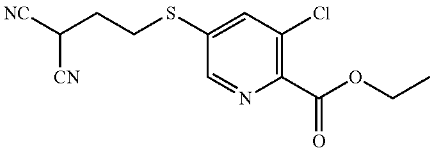 [SMILES: CCOC(=O)c1ncc(SCCC(C#N)C#N)cc1Cl]

To a solution of ethyl 3,5-dichloropyridine-2-carboxylate (0.2 g, 0.861 mmol) and 5-amino-2,3-dihydrothiophene-4-carbonitrile (0.118 g, 96.3% w/w purity, 0.904 mmol) in DMF (3.4 mL) cooled at −20° C. was added dropwise a solution of Sodium bis(trimethylsilyl)amide (1M in THF, 1.9 mL, 1.9 mmol). The reaction mixture was stirred at this temperature for 1 h, then quenched with aqueous saturated ammonium chloride (5 mL) and extracted three times with TBME (3×20 mL). The combined organic layers were washed twice with brine (2×10 mL), dried over solid Sodium sulfate, filtered and evaporated under reduced pressure yielding a dark oil (0.296 g). QNMR indicated a strength of 37% w/w, leading to a chemical yield of 41%. $^1$H NMR (400 MHz, CDCl3) δ ppm 1.44 (t, J=7.15 Hz, 3H) 2.36-2.42 (m, 2H) 3.28 (t, J=7.15 Hz, 2H) 4.17 (t, J=7.15 Hz, 1H) 4.45-4.51 (q, 2H) 7.76 (d, J=2.20 Hz, 1H) 8.49 (d, J=1.83 Hz, 1H) LC-MS: ret.: 0.93 min, m/z $+H^+$: 310/312

Example 18: Preparation of 5-(3,3-dicyanopropylsulfanyl)-3-ethylsulfanyl-pyridine-2-carboxylic acid

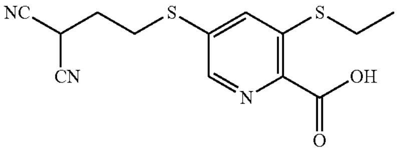 [SMILES: CCSc1cc(SCCC(C#N)C#N)cnc1C(=O)O]

To a solution of 5-chloro-3-ethylsulfanyl-pyridine-2-carboxylic acid (1.5 g, 92% w/w purity, 6.65 mmol) and 5-amino-2,3-dihydrothiophene-4-carbonitrile (1.1 g, 94.3% w/w purity, 8.25 mmol) in DMF (25 mL) was added a solution of Lithium bis(trimethylsilyl)amide (1M in THF, 19 mL, 19 mmol) over a period of 30 min at room temperature. The reaction mixture was stirred at this temperature for 1 h. It was then quenched with aqueous 1N aqueous HCl (22 ml) extracted three times with ethyl acetate (3×100 mL). The combined organic layers were washed twice brine (2×50 mL), dried over solid Sodium sulfate, filtered and evaporated under reduced pressure yielding an oil which solidified over time (2.582 g). QNMR indicated a strength of 70% w/w, leading to a chemical yield of 92%.

Alternatively, the title product can be obtained using the following protocol:

Solid sodium tert-butoxide (19.3 g, 97% w/w, 195 mmol) was suspended in NMP (65 mL), the mixture was then stirred at 67° C. until a turbid solution was formed. To this solution, a mixture of 5-chloro-3-ethylsulfanyl-pyridine-2-carboxylic acid (15 g, 94.1% w/w purity, 64.8 mmol) and 5-amino-2,3-dihydrothiophene-4-carbonitrile (10.3 g, 95.4% w/w purity, 77.8 mmol) in NMP (65 mL) was added dropwise over a period of 1 h. After addition, solid sodium tert-butoxide (3.21 g, 97% w/w, 32.4 mmol) was added and the mixture stirred for 1.5 h, before being cooled down to room temperature. 150 mL of 1M aq. NaOH was added and the mixture was stirred for 10 minutes before being diluted with 100 mL of TBME (tert-butyl-methyl-ether). The phases were separated and the aqueous phase, containing the desired product, was acidified with 4N aq. HCl until a pH of 1.5 to 1 was reached. The aqueous phase was extracted three times with EtOAc (3×150 mL). The combined organic layers (from EtOAc) were dried over solid anhydrous sodium sulfate and concentrated under reduced pressure to give a crude solution (57.57 g) of desired product 5-(3,3-dicyanopropylsulfanyl)-3-ethylsulfanyl-pyridine-2-carboxylic acid in residual NMP. Quantification led to a measurement of 32% w/w purity in NMP, leading to a chemical yield of 92.4%.

1H NMR (400 MHz, d6-DMSO) δ ppm 1.25 (t, J=7.34 Hz, 3H) 2.36 (q, J=7.09 Hz, 2H) 3.02 (q, J=7.34 Hz, 2H) 3.30 (dd, J=8.44, 6.60 Hz, 2H) 4.92 (t, J=6.97 Hz, 1H) 7.70 (d, J=2.20 Hz, 1H) 8.33 (d, J=2.20 Hz, 1H) 13.12 (br s, 1H) LC-MS: m/z +H+: 308

Example 19: Preparation of 3-chloro-5-(3,3-dicyanopropylsulfanyl)pyridine-2-carboxylic acid

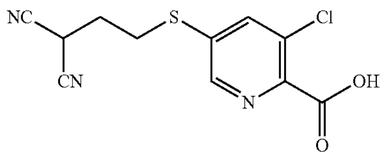 [SMILES: N#CC(C#N)CCSc1cnc(C(=O)O)c(Cl)c1]

To a solution of 5-bromo-3-chloro-pyridine-2-carboxylic acid (0.3 g, 1.27 mmol) and 5-amino-2,3-dihydrothiophene-4-carbonitrile (0.165 g, 1.307 mmol) in DMF (2.5 mL) cooled at −20° C. was added dropwise a solution of Sodium bis(trimethylsilyl)amide (1M in THF, 1.9 mL, 1.9 mmol). The reaction mixture was stirred at room temperature for 3 h, then quenched with aqueous saturated ammonium chloride (5 mL), pH was adjusted to 1 by addition of aq. 2N HCl, and this was extracted three times with ethyl acetate (3×20 mL). The combined organic layers were washed twice with brine (2×10 mL), dried over solid Sodium sulfate, filtered and evaporated under reduced pressure yielding a dark oil (0.456 g). QNMR indicated a strength of 35% w/w, leading to a chemical yield of 44%. $^1$H NMR (400 MHz, d6-DMSO) δ ppm 2.32-2.41 (m, 2H) 3.29 (dd, J=8.25, 6.79 Hz, 2H) 4.91 (t, J=6.97 Hz, 1H) 8.10 (d, J=1.83 Hz, 1H) 8.53 (d, J=1.83 Hz, 1H) 13.44-13.99 (m, 1H) 13.69 (s, 1H) LC-MS: m/z +H$^+$: 282/284

Example 20: Preparation of 5-(3,3-dicyanopropylsulfanyl)-3-ethylsulfanyl-pyridine-2-carboxamide

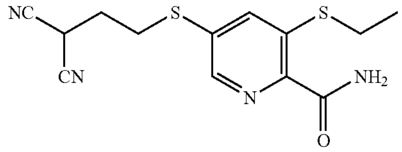 [SMILES: CCSc1cc(SCCC(C#N)C#N)cnc1C(N)=O]

To a solution of 5-chloro-3-ethylsulfanyl-pyridine-2-carboxamide (0.2 g, 98% purity w/w, 0.905 mmol) and 5-amino-2,3-dihydrothiophene-4-carbonitrile (0.156 g, 95% purity w/w, 1.18 mmol) in DMF (3.6 mL) was added Sodium tert-butoxide (0.358 g, 3.62 mmol). The reaction mixture was stirred at room temperature for 2 h, then quenched by pouring onto ice/water, and this was extracted three times with ethyl acetate. The combined organic layers were dried over solid Sodium sulfate, filtered and evaporated under reduced pressure yielding a pale yellow solid (0.319 g). Ethyl acetate was added to the solid, this solid was then triturated and ethyl acetate was removed by filtration. The white solid was collected (94 mg), leading to a chemical yield of 34%. $^1$H NMR (400 MHz, d6-DMSO) δ ppm 1.26 (t, J=7.34 Hz, 3H) 2.36 (q, J=6.97 Hz, 2H) 2.95 (q, J=7.34 Hz, 2H) 3.28 (m, 2H) 4.93 (t, J=6.97 Hz, 1H) 7.51 (bs, 1H) 7.66 (d, J=1.47 Hz, 1H) 7.95 (bs, 1H) 8.28 (d, J=1.47 Hz, 1H)

Example 21: Preparation of 5-(3-cyano-2-imino-tetrahydrothiophen-3-yl)-3-ethylsulfanyl-pyridine-2-carboxylic acid

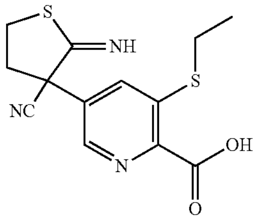 [SMILES: CCSc1cc(C2(C#N)CCSC2=N)cnc1C(=O)O]

To a solution of 5-(1-cyanocyclopropyl)-3-ethylsulfanyl-pyridine-2-carboxylic acid (1 g, 4.027 mmol), acetic acid (0.048 g, 0.805 mmol), tetrabutylammonium bromide (0.26 g, 0.805 mmol) in DMF (8 mL) was added potassium thiocyanate (1.96 g, 20.14 mmol). The mixture was stirred overnight at 85° C., then 3 h at 105° C. before being cooled down to room temperature. The reaction mixture was then poured into an acetonitrile:water mixture containing 0.1% of acetic acid. The solvent was evaporated yielding a brownish wax (6.782 g). To 1 g of this wax was added aqueous acetonitrile and ethyl acetate, the upper layer was decanted off and washed three times with ethyl acetate. The oil was then dried under reduced pressure. $^1$H NMR (400 MHz, d6-DMSO) δ ppm 1.19 (t, J=7.34 Hz, 3H) 2.89 (m, 3H) 3.01 (dt, J=11, 5.14 Hz, 1H) 3.17 (m, 1H) 3.40 (dt, J=11.37, 5.87 Hz, 1H) 7.69 (d, J=2.2 Hz, 1H) 8.38 (d, J=1.8 Hz, 1H) 11.31 (s, 1H)

Example 22: Preparation of 5-(1-cyano-3-thiocyanato-propyl)-3-ethylsulfanyl-pyridine-2-carboxylic acid

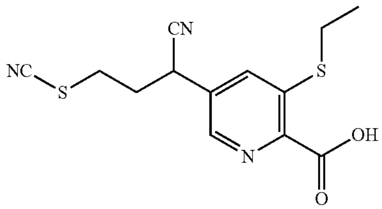 [SMILES: CCSc1cc(C(C#N)CCSC#N)cnc1C(=O)O]

To a solution of 5-(1-cyanocyclopropyl)-3-ethylsulfanyl-pyridine-2-carboxylic acid (1.5 g, 73.1% w/w purity, 4.4 mmol), dissolved in dioxane (6.6 mL), acetic acid (6.6 mL) was added Hydrochloric acid (1M in dioxane, 4.4 mL, 4.4 mmol). The reaction was stirred overnight at 75° C., before being allowed to cool down to room temperature. 10 mL of 2N aq. HCl were added, 20 mL of EtOAc were added, and the phases separated. The aqueous phase was extracted twice with 20 mL of EtOAc, combined, dried over solid Sodium sulfate, filtered and evaporated under reduced pressure yielding a brown oil (1.5525 g).

The crude 5-(3-chloro-1-cyano-propyl)-3-ethylsulfanyl-pyridine-2-carboxylic acid obtained (purity measured 63.3%; chemical yield 78%) was then purified by column chromatography; the purity was then increased to 86.7% w/w. 0.65 g of this product 5-(3-chloro-1-cyano-propyl)-3-ethylsulfanyl-pyridine-2-carboxylic acid (86.7% w/w pure, 1.98 mmol) were then dissolved in DMF (5.94 mL); potassium thiocyanate (0.5 g, 5.14 mmol) was added and the reaction mixture was heated at 70° C. overnight. Extra potassium thiocyanate (0.25 g, 2.57 mmol) were added and the reaction mixture was stirred 4 h at 70° C. before being allowed to cool down to room temperature. The mixture was acidified to pH 1 with 2N aq. HCl and extracted three times with EtOAc (3x30 mL). The combined organic layers were then dried over anhydrous sodium sulfate, filtered and evaporated under reduced pressure yielding a brown oil (1.2157 g). QNMR indicated a purity of 74.2% w/w, the desired title compound was then obtained with a chemical yield of 74%. $^1H$ NMR (400 MHz, d6-DMSO) δ ppm 1.25-1.30 (m, 3H) 2.33-2.44 (m, 1H) 2.52-2.58 (m, 1H) 3.03 (q, J=7.34 Hz, 2H) 3.14-3.20 (m, 2H) 4.60 (dd, J=8.07, 6.60 Hz, 1H) 7.93 (d, J=1.83 Hz, 1H) 8.46 (d, J=1.83 Hz, 1H) LC-MS: m/z $+H^+$: 308

Example 23: Preparation of 5-(1-cyanocyclopropyl)-N-methyl-pyridine-2-carboxamide

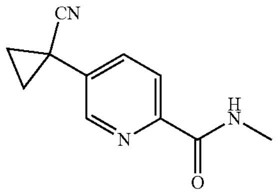

To a solution of 5-chloro-N-methyl-pyridine-2-carboxamide (0.1 g, 0.584 mmol), 5-amino-2,3-dihydrothiophene-4-carbonitrile (0.78 g, 94% w/w purity, 0.584 mmol) in DMF (4.67 mL) is added a 2M THF solution of sodium tertiobutanolate (0.64 mL, 1.28 mmol). The reaction mixture is heated at 70° C. overnight, then cooled down to room temperature. 10 mL of an aqueous saturated NH4Cl solution is added into the mixture, which is then acidified by 10 mL of 1N aq. HCl. The mixture is extracted three times with EtOAc (3x20 mL), the combined organic layers are washed with 10 mL of sat. aq. NaHCO3, then twice with 10 mL of brine. The combined organic layers are then dried over anhydrous magnesium sulfate and concentrated under reduced pressure, giving 0.1 g of an orange oil. The crude is then purified by column chromatography, affording 30.1 mg of 5-(1-cyanocyclopropyl)-N-methyl-pyridine-2-carboxamide under the form of a white solid (isolated yield of 25%). 1H NMR (400 MHz, $CDCl_3$) δ ppm 1.45-1.57 (m, 2H) 1.84-1.92 (m, 2H) 3.06 (d, J=5.09 Hz, 3H) 7.70 (dd, J=8.17, 2.36 Hz, 1H) 7.96 (br s, 1H) 8.20 (d, J=7.99 Hz, 1H) 8.57 (d, J=2.18 Hz, 1H)

The invention claimed is:

1. A process for the preparation of a compound of formula I:

(I)

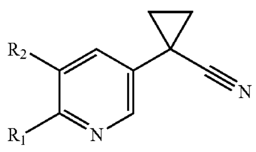

wherein $R_1$ is $—CO_2R_4$, $—CO(NR_5R_6)$, carboxylate or cyano; $R_2$ is hydrogen, halogen or $—SR_3$; $R_3$ is $C_1$-$C_4$alkyl or $C_3$-$C_6$cycloalkyl-$C_1$-$C_4$alkyl; $R_4$ is hydrogen, $—Si(CH_3)_3$ or $C_1$-$C_6$alkyl; and $R_5$ and $R_6$ are, independently from each other, hydrogen or $C_1$-$C_4$alkyl, or an agrochemically acceptable salt of a compound of formula I;

the process comprises:

reacting a compound of formula (III)

(III)

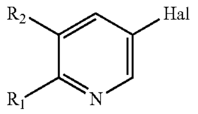

wherein $R_1$ and $R_2$ are defined as under formula I above and Hal is a halogen; with a compound of formula (IV), (IV)

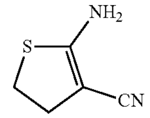

in the presence of a suitable base, in an appropriate solvent or a diluent;

to produce a compound of formula (I) or an agrochemically acceptable salt thereof.

2. The process according to claim 1, wherein $R_1$ is $—CO_2R_4$, $—CONH_2$, carboxylate or a cyano group; and $R_4$ is hydrogen, $—Si(CH_3)_3$, methyl, ethyl, isopropyl, tert-butyl, or sec-butyl.

3. The process according to claim 2, wherein $R_1$ is $—CO_2H$ or carboxylate.

4. The process according to claim 1, wherein $R_2$ is hydrogen, chloro or $—SR_3$; wherein $R_3$ is ethyl.

5. The process according to claim 4, wherein $R_2$ is —S-ethyl.

6. The process according to claim 1, wherein Hal is chloro or bromo.

7. The process according to claim 1, wherein the suitable base is selected from sodium hydroxide, potassium hydroxide, sodium tertiobutanolate, and potassium tertiobutanolate.

8. The process according to claim 1, wherein the solvent or the diluent is selected from dimethylformamide, dimethylsulfoxide, N-methyl-pyrrolidine, dimethylacetamide, sulfolane and N,N'-dimethylpropyleneurea (DMPU).

9. The process according to claim 1, which is carried out in a temperature range from approximately 0° C. to approximately +100° C.

10. The process according to claim 1, wherein, when $R_1$ is a carboxylate anion, the suitable base is selected from magnesium bis(tertio-butanolate) and magnesium bis(hexamethyldisilazide).

11. The process according to claim 1, wherein, when $R_1$ is a carboxylate anion, the suitable base is selected from sodium hydroxide, potassium hydroxide, sodium tertiobutanolate, and potassium tertiobutanolate, and wherein the process further comprises addition of magnesium$^{(II)}$, zinc$^{(II)}$ or Al$^{(III)}$ salts as additives following in situ formation of a compound of formula (INT I)

INT I

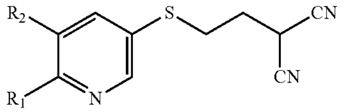

wherein $R_1$ and $R_2$ are as defined in formula I in claim 1.

12. The process according to claim 11, wherein the magnesium$^{(II)}$, zinc$^{(II)}$ or $Al^{(III)}$ salts are selected from $MgCl_2$, $ZnCl_2$, $Al(OtBu)_3$ and $AlCl_3$.

13. The process according to claim 1, wherein, when $R_1$ is a carboxylate anion, the suitable base is selected from sodium hydroxide, potassium hydroxide, sodium tertiobutanolate, and potassium tertiobutanolate, and wherein the process further comprises addition of trimethylsilylchloride after distillation of the water or alcohol generated during the in situ formation of a compound of formula (INT I)

INT I

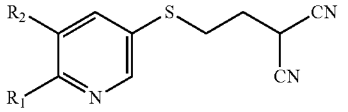

wherein $R_1$ and $R_2$ are as defined in formula I in claim 1.

14. A compound of formula (INT I)

INT I

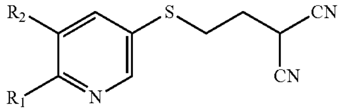

wherein $R_1$ is —$CO_2R_4$, —$CO(NR_5R_6)$ or cyano; $R_2$ is hydrogen, halogen or —$SR_3$; $R_3$ is $C_1$-$C_4$alkyl or $C_3$-$C_6$cycloalkyl-$C_1$-$C_4$alkyl; $R_4$ is hydrogen, —$Si(CH_3)_3$ or $C_1$-$C_6$alkyl; and $R_5$ and $R_6$ are, independently from each other, hydrogen or $C_1$-$C_4$alkyl; or an agrochemically acceptable salt of a compound of formula INT I.

15. A compound of formula (INT II)

INT II

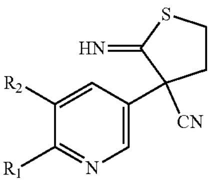

wherein $R_1$ is —$CO_2R_4$, —$CO(NR_5R_6)$ or cyano; $R_2$ is hydrogen, halogen or —$SR_3$; $R_3$ is $C_1$-$C_4$alkyl or $C_3$-$C_6$cycloalkyl-$C_1$-$C_4$alkyl; $R_4$ is hydrogen, —$Si(CH_3)_3$ or $C_1$-$C_6$alkyl; and $R_5$ and $R_6$ are, independently from each other, hydrogen or $C_1$-$C_4$alkyl; or an agrochemically acceptable salt of a compound of formula INT II.

16. A compound of formula (INT III)

INT III

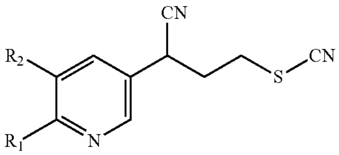

wherein $R_1$ is —$CO_2R_4$, —$CO(NR_5R_6)$ or cyano; $R_2$ is hydrogen, halogen or —$SR_3$; $R_3$ is $C_1$-$C_4$alkyl or $C_3$-$C_6$cycloalkyl-$C_1$-$C_4$alkyl; $R_4$ is hydrogen, —$Si(CH_3)_3$ or $C_1$-$C_6$alkyl; and $R_5$ and $R_6$ are, independently from each other, hydrogen or $C_1$-$C_4$alkyl; or an agrochemically acceptable salt of a compound of formula INT III.

17. A compound according to claim 14, wherein $R_1$ is —$CO_2R_4$, —$CONH_2$ or cyano; wherein $R_4$ is hydrogen, —$Si(CH_3)_3$, methyl, ethyl, isopropyl, tert-butyl, or sec-butyl; and $R_2$ is hydrogen, chloro or —$SR_3$; wherein $R_3$ is ethyl.

18. A compound of formula INT I according to claim 14, selected from the group consisting of:

2-[2-[(6-cyano-5-ethylsulfanyl-3-pyridyl)sulfanyl]ethyl]propanedinitrile (example 14);

methyl 5-(3,3-dicyanopropylsulfanyl)-3-ethylsulfanyl-pyridine-2-carboxylate (example 15); ethyl 5-(3,3-dicyanopropylsulfanyl)-3-ethylsulfanyl-pyridine-2-carboxylate (example 16);

ethyl 3-chloro-5-(3,3-dicyanopropylsulfanyl)pyridine-2-carboxylate (example 17);

5-(3,3-dicyanopropylsulfanyl)-3-ethylsulfanyl-pyridine-2-carboxylic acid (example 18);

3-chloro-5-(3,3-dicyanopropylsulfanyl)pyridine-2-carboxylic acid (example 19); and 5-(3,3-dicyanopropylsulfanyl)-3-ethylsulfanyl-pyridine-2-carboxamide (example 20).

19. A process for the preparation of a compound of formula I:

(I)

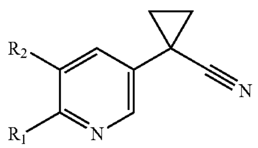

wherein $R_1$ is —$CO_2R_4$, —$CO(NR_5R_6)$, carboxylate or cyano; $R_2$ is hydrogen, halogen or —$SR_3$; $R_3$ is $C_1$-$C_4$alkyl or $C_3$-$C_6$cycloalkyl-$C_1$-$C_4$alkyl; $R_4$ is hydrogen, —$Si(CH_3)_3$ or $C_1$-$C_6$alkyl; and $R_5$ and $R_6$ are, independently from each other, hydrogen or $C_1$-$C_4$alkyl, or an agrochemically acceptable salt of a compound of formula I;

the process comprises:

reacting a compound of formula (INT I)

INT I

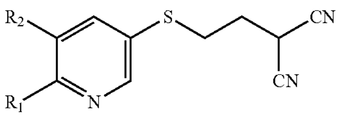

wherein $R_1$ and $R_2$ are defined as under formula I above;

in the presence of a suitable base, in an appropriate solvent or a diluent;

to produce a compound of formula (I) or an agrochemically acceptable salt thereof.

20. The process according to claim 1, being carried out at a temperature from approximately +20° C. to approximately +80° C.

* * * * *